(12) United States Patent
Wallace

(10) Patent No.: US 9,375,223 B2
(45) Date of Patent: Jun. 28, 2016

(54) METHODS AND DEVICES FOR ENDOVASCULAR THERAPY

(71) Applicant: Michael P Wallace, Pleasanton, CA (US)

(72) Inventor: Michael P Wallace, Pleasanton, CA (US)

(73) Assignee: CardioProlific Inc., Reno, NV (US)

( * ) Notice: Subject to any disclaimer, the term of this patent is extended or adjusted under 35 U.S.C. 154(b) by 8 days.

(21) Appl. No.: 14/164,512

(22) Filed: Jan. 27, 2014

(65) Prior Publication Data

US 2014/0142494 A1   May 22, 2014

Related U.S. Application Data

(63) Continuation-in-part of application No. 13/962,646, filed on Aug. 8, 2013, which is a continuation-in-part of application No. 13/625,405, filed on Sep. 24, 2012, which is a continuation-in-part of application No. 13/438,221, filed on Apr. 3, 2012, which is a continuation-in-part of application No. 13/134,470, filed on Jun. 8, 2011, now abandoned, which is a continuation-in-part of application No. 12/930,415, filed on Jan. 6, 2011, which is a continuation-in-part of application No. 12/925,495, filed on Oct. 22, 2010, now abandoned, which is a continuation-in-part of application No. 12/807,129, filed on Aug. 27, 2010, now abandoned, which is a continuation-in-part of application No. 12/661,853, filed on Mar. 25, 2010, now abandoned.

(60) Provisional application No. 61/278,353, filed on Oct. 6, 2009.

(51) Int. Cl.
| | |
|---|---|
| *A61B 17/22* | (2006.01) |
| *A61M 37/00* | (2006.01) |
| *A61B 17/32* | (2006.01) |
| *A61B 18/00* | (2006.01) |
| *A61B 18/24* | (2006.01) |
| *A61B 18/02* | (2006.01) |

(52) U.S. Cl.
CPC ....... *A61B 17/2202* (2013.01); *A61B 17/22004* (2013.01); *A61B 17/22012* (2013.01); *A61M 37/0092* (2013.01); *A61B 18/245* (2013.01); *A61B 2017/22014* (2013.01); *A61B 2017/22015* (2013.01); *A61B 2017/22018* (2013.01); *A61B 2017/22039* (2013.01); *A61B 2017/22082* (2013.01); *A61B 2017/22088* (2013.01); *A61B 2017/22098* (2013.01); *A61B 2017/320088* (2013.01); *A61B 2018/00029* (2013.01); *A61B 2018/0212* (2013.01)

(58) Field of Classification Search
CPC .............. A61B 17/22012; A61B 17/22004; A61B 17/2202; A61B 2017/22014; A61B 2017/22082; A61B 2017/22088; A61B 2017/22015; A61B 2017/22018; A61B 2017/22039; A61B 2017/320088; A61B 2018/0212; A61B 2017/22098; A61B 18/02; A61B 18/24; A61B 18/245; A61B 2017/00853; A61B 2017/00867; A61B 2017/1107; A61B 2017/1139; A61B 2017/22084; A61B 8/485; A61M 37/0092; A61M 25/00; A61M 25/104; A61N 2007/0043
USPC ............... 604/20–22, 96.01, 101.01, 101.03, 604/101.05, 102.01, 102.02, 102.03, 604/103.01, 103.02; 601/2; 607/96–99; 606/159
See application file for complete search history.

(56) References Cited

U.S. PATENT DOCUMENTS

| | | | |
|---|---|---|---|
| 4,698,058 A | 10/1987 | Greenfeld et al. | |
| 5,127,902 A * | 7/1992 | Fischell | 604/22 |

(Continued)

*Primary Examiner* — Kevin C Sirmons
*Assistant Examiner* — William Carpenter
(74) *Attorney, Agent, or Firm* — Raymond Sun

(57) ABSTRACT

The present invention provides methods and devices for treating endovascular disease. Vibrational energy is delivered to change compliance and increase permeability at the treatment area. To improve clinical outcomes, one or more therapeutic drugs may be delivered to the treatment area.

17 Claims, 13 Drawing Sheets

(56) References Cited

U.S. PATENT DOCUMENTS

| | | | |
|---|---|---|---|
| 5,197,946 A | 3/1993 | Tachibana et al. | |
| 5,362,309 A | 11/1994 | Carter | |
| 5,399,158 A | 3/1995 | Lauer et al. | |
| 5,445,155 A | 8/1995 | Sieben | |
| 5,474,531 A * | 12/1995 | Carter | 604/22 |
| 5,620,409 A | 4/1997 | Venuto et al. | |
| 5,632,754 A * | 5/1997 | Farley et al. | 606/159 |
| 5,709,676 A | 1/1998 | Alt | |
| 5,713,847 A | 2/1998 | Howard et al. | |
| 5,725,494 A * | 3/1998 | Brisken | 604/22 |
| 5,728,062 A | 3/1998 | Brisken | |
| 5,735,811 A * | 4/1998 | Brisken | A61B 17/22012 604/22 |
| 5,846,218 A * | 12/1998 | Brisken et al. | 604/22 |
| 5,927,277 A | 7/1999 | Baudino et al. | |
| 5,931,805 A * | 8/1999 | Brisken | 604/22 |
| 5,941,896 A * | 8/1999 | Kerr | 606/200 |
| 5,957,882 A | 9/1999 | Nita et al. | |
| 5,971,949 A * | 10/1999 | Levin et al. | 604/22 |
| 5,980,566 A * | 11/1999 | Alt et al. | 623/23.7 |
| 5,980,950 A | 11/1999 | Porter | |
| 5,997,497 A * | 12/1999 | Nita et al. | 604/22 |
| 6,001,069 A | 12/1999 | Tachibana et al. | |
| 6,002,961 A | 12/1999 | Mitragotri et al. | |
| 6,019,724 A | 2/2000 | Gronningsaeter et al. | |
| 6,024,718 A * | 2/2000 | Chen et al. | 604/22 |
| 6,028,066 A | 2/2000 | Unger | |
| 6,066,123 A | 5/2000 | Li et al. | |
| RE36,939 E | 10/2000 | Tachibana et al. | |
| 6,135,976 A | 10/2000 | Tachibana et al. | |
| 6,176,842 B1 * | 1/2001 | Tachibana et al. | 604/22 |
| 6,190,323 B1 | 2/2001 | Dias et al. | |
| 6,210,393 B1 * | 4/2001 | Brisken | A61N 7/022 128/898 |
| 6,221,038 B1 | 4/2001 | Brisken | |
| 6,228,046 B1 | 5/2001 | Brisken | |
| 6,287,272 B1 | 9/2001 | Brisken et al. | |
| 6,296,619 B1 * | 10/2001 | Brisken et al. | 604/22 |
| 6,308,714 B1 | 10/2001 | Siegel et al. | |
| 6,361,554 B1 | 3/2002 | Brisken | |
| 6,368,330 B1 | 4/2002 | Hynes et al. | |
| 6,372,498 B2 | 4/2002 | Newman et al. | |
| 6,387,116 B1 | 5/2002 | McKenzie et al. | |
| 6,432,068 B1 | 8/2002 | Corl et al. | |
| 6,464,660 B2 * | 10/2002 | Brisken et al. | 604/22 |
| 6,464,680 B1 | 10/2002 | Brisken et al. | |
| 6,484,052 B1 | 11/2002 | Visuri et al. | |
| 6,494,874 B1 | 12/2002 | Brisken | |
| 6,503,243 B1 | 1/2003 | Brisken | |
| 6,508,775 B2 | 1/2003 | McKenzie et al. | |
| 6,524,271 B2 | 2/2003 | Brisken | |
| 6,575,956 B1 | 6/2003 | Brisken et al. | |
| 6,626,902 B1 | 9/2003 | Kucharczyk et al. | |
| 6,659,949 B1 | 12/2003 | Lang et al. | |
| 6,689,086 B1 | 2/2004 | Nita et al. | |
| 6,716,412 B2 | 4/2004 | Unger | |
| 6,723,063 B1 | 4/2004 | Zhang et al. | |
| 6,733,451 B2 | 5/2004 | Rabiner | |
| 6,755,853 B2 | 6/2004 | McKenzie et al. | |
| 6,794,369 B2 | 9/2004 | Newman et al. | |
| 7,037,267 B1 | 5/2006 | Lipson et al. | |
| 7,413,556 B2 | 8/2008 | Zhang et al. | |
| 7,517,328 B2 | 4/2009 | Hoffmann | |
| 7,914,509 B2 | 3/2011 | Bennett | |
| 2001/0031243 A1 | 10/2001 | Unger | |
| 2002/0062078 A1 | 5/2002 | Crutchfield et al. | |
| 2003/0060711 A1 | 3/2003 | Michaeli | |
| 2004/0049134 A1 | 3/2004 | Tosaya et al. | |
| 2004/0097996 A1 | 5/2004 | Rabiner et al. | |
| 2004/0138562 A1 | 7/2004 | Makower et al. | |
| 2004/0138563 A1 | 7/2004 | Moehring et al. | |
| 2004/0143322 A1 * | 7/2004 | Litvack et al. | 623/1.42 |
| 2004/0153009 A1 | 8/2004 | Horzewski et al. | |
| 2005/0038008 A1 | 2/2005 | Ikari | |
| 2005/0038342 A1 | 2/2005 | Mozayeni et al. | |
| 2005/0038376 A1 * | 2/2005 | Zumeris | A61L 2/02 604/22 |
| 2005/0124897 A1 | 6/2005 | Chopra | |
| 2005/0187513 A1 * | 8/2005 | Rabiner et al. | 604/22 |
| 2005/0209642 A1 | 9/2005 | Palti | |
| 2005/0215946 A1 | 9/2005 | Hansmann et al. | |
| 2006/0020239 A1 | 1/2006 | Geiger | |
| 2006/0058627 A1 | 3/2006 | Flaherty et al. | |
| 2006/0079773 A1 | 4/2006 | Mourad et al. | |
| 2006/0173387 A1 | 8/2006 | Hansmann | |
| 2006/0206028 A1 | 9/2006 | Lee et al. | |
| 2006/0235349 A1 | 10/2006 | Osborn | |
| 2007/0005121 A1 | 1/2007 | Khanna | |
| 2007/0060882 A1 * | 3/2007 | Tal | 604/102.01 |
| 2007/0265560 A1 * | 11/2007 | Soltani | A61B 17/2202 604/22 |
| 2008/0038008 A1 | 2/2008 | Fujita et al. | |
| 2008/0045896 A1 * | 2/2008 | Yribarren et al. | 604/103.1 |
| 2008/0154173 A1 | 6/2008 | Burnett | |
| 2008/0154181 A1 | 6/2008 | Khanna | |
| 2008/0243049 A1 | 10/2008 | Hardy | |
| 2008/0294089 A1 | 11/2008 | Hardy | |
| 2008/0299177 A1 | 12/2008 | Hardy | |
| 2008/0312581 A1 | 12/2008 | Hardy | |
| 2008/0319375 A1 | 12/2008 | Hardy | |
| 2008/0319376 A1 | 12/2008 | Wilcox | |
| 2011/0105960 A1 * | 5/2011 | Wallace | 601/2 |
| 2012/0215099 A1 * | 8/2012 | Wallace | 600/431 |
| 2013/0023897 A1 * | 1/2013 | Wallace | 606/128 |
| 2013/0345617 A1 * | 12/2013 | Wallace | 604/22 |

\* cited by examiner

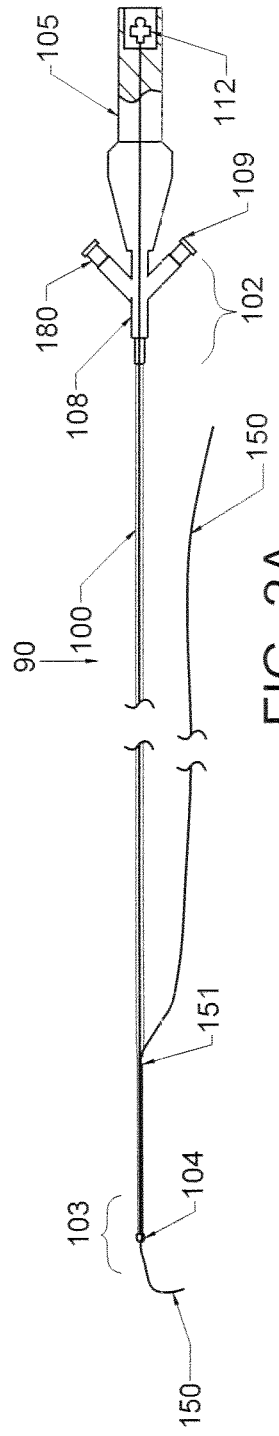
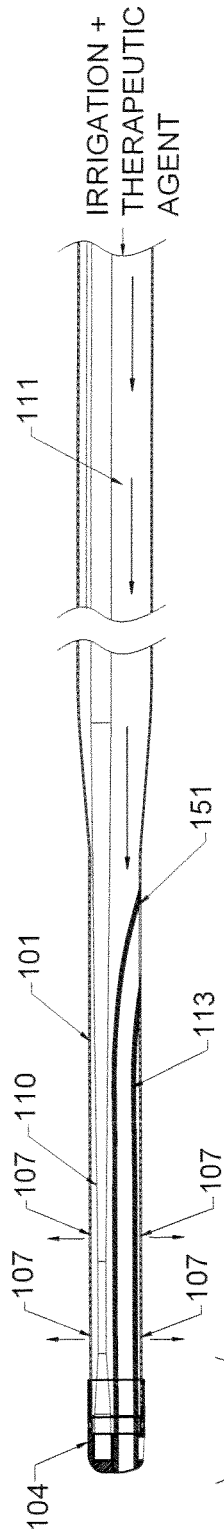
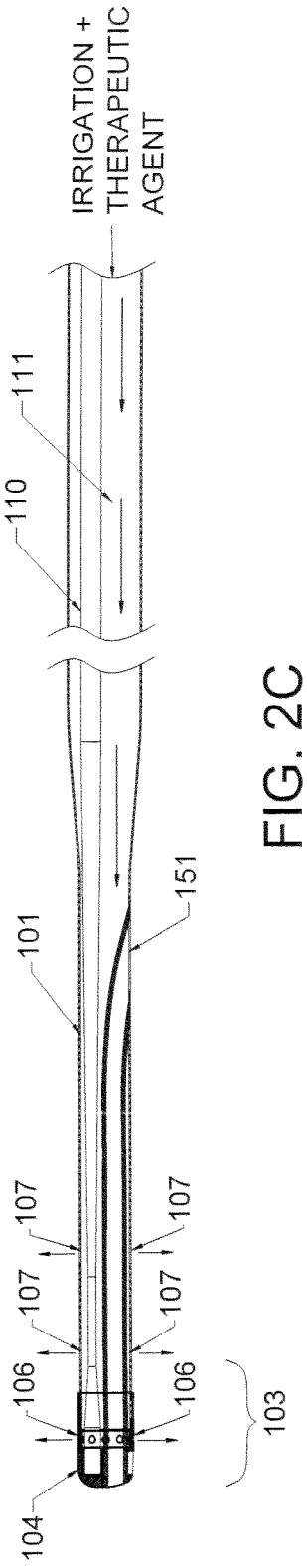
FIG. 2A
FIG. 2B
FIG. 2C

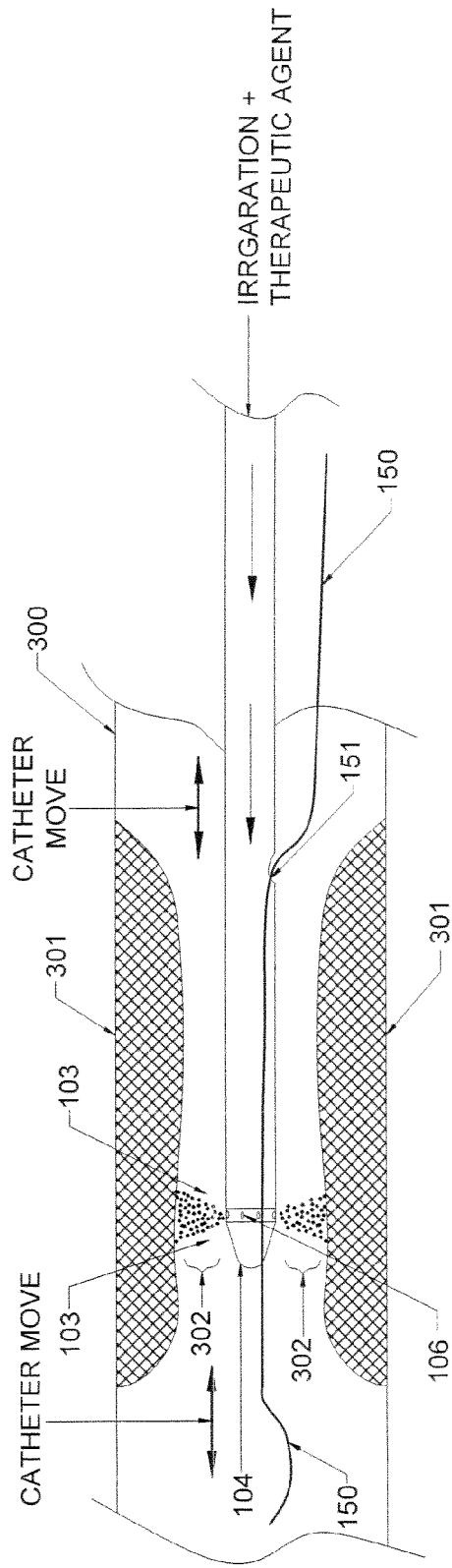
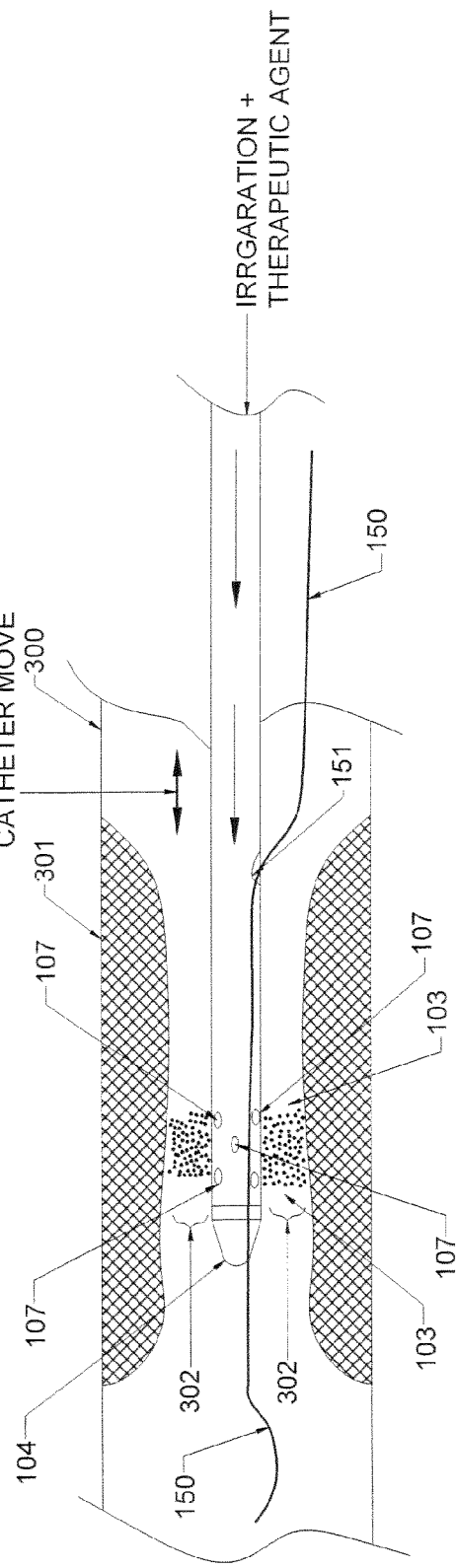

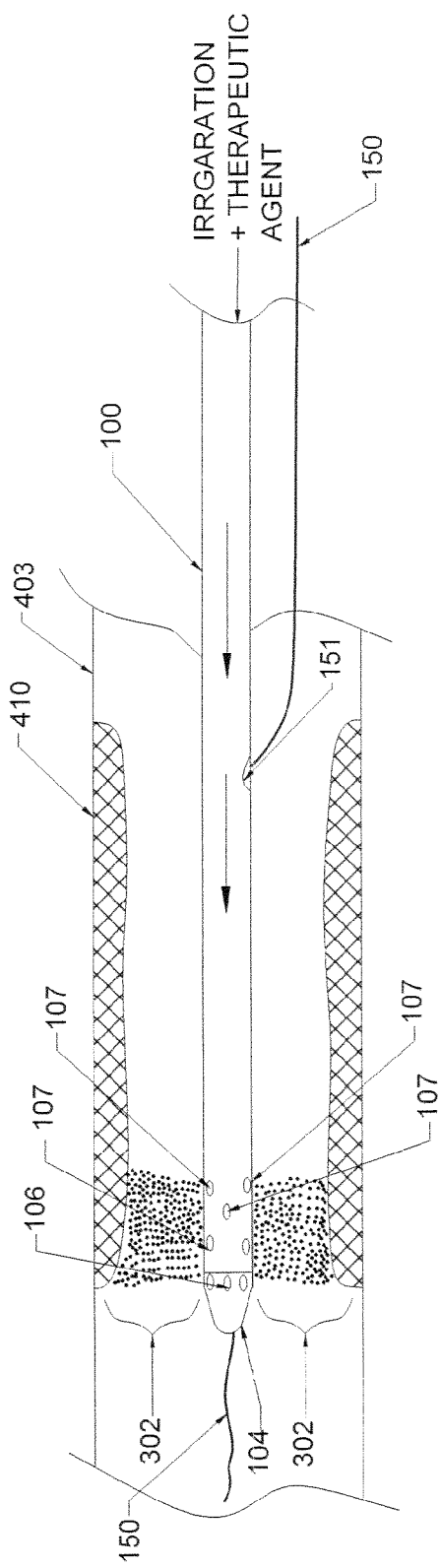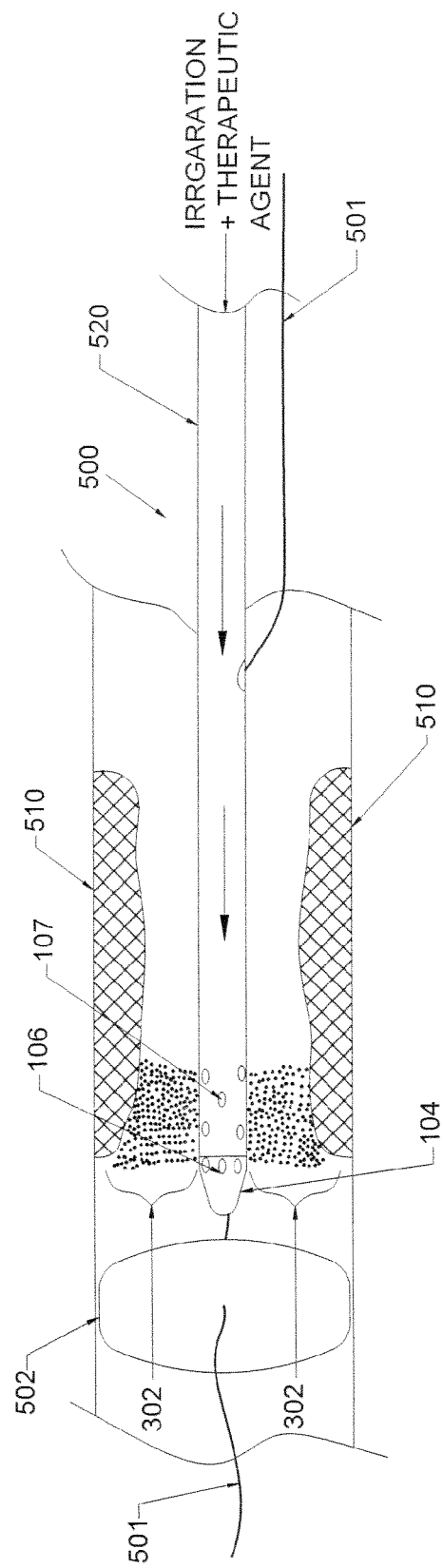

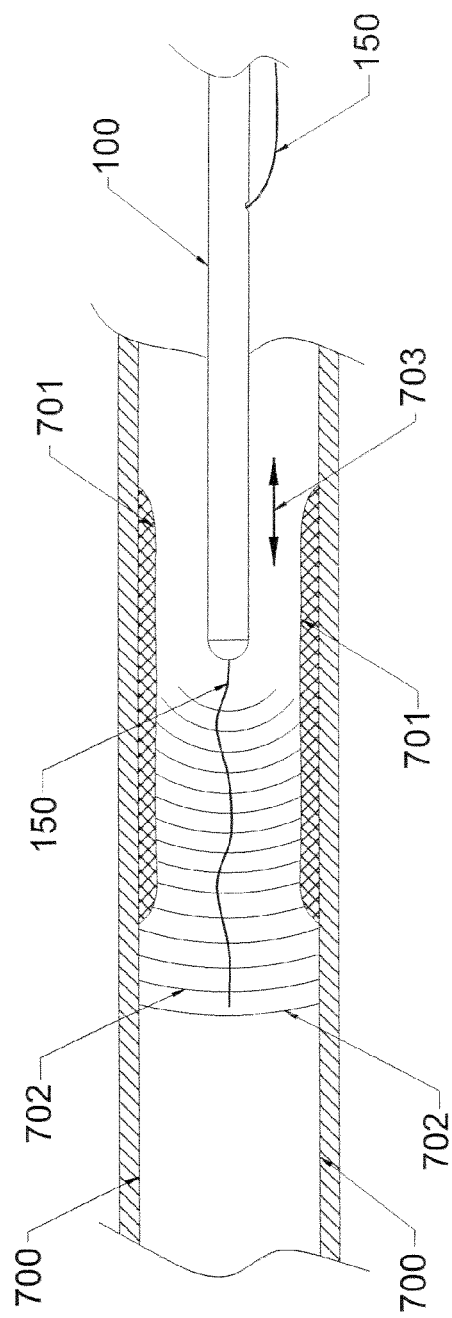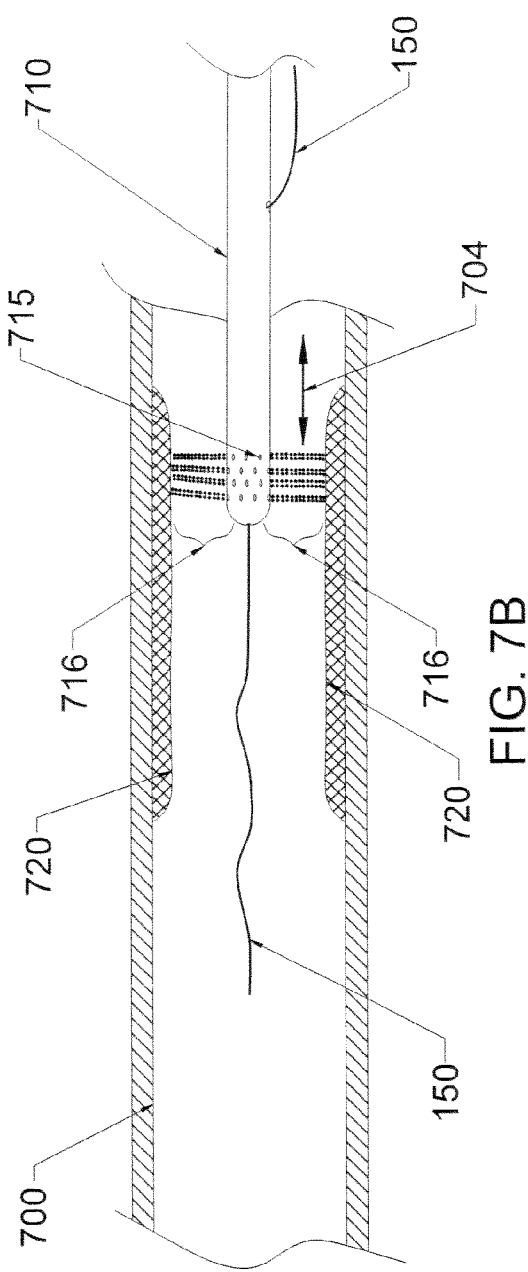

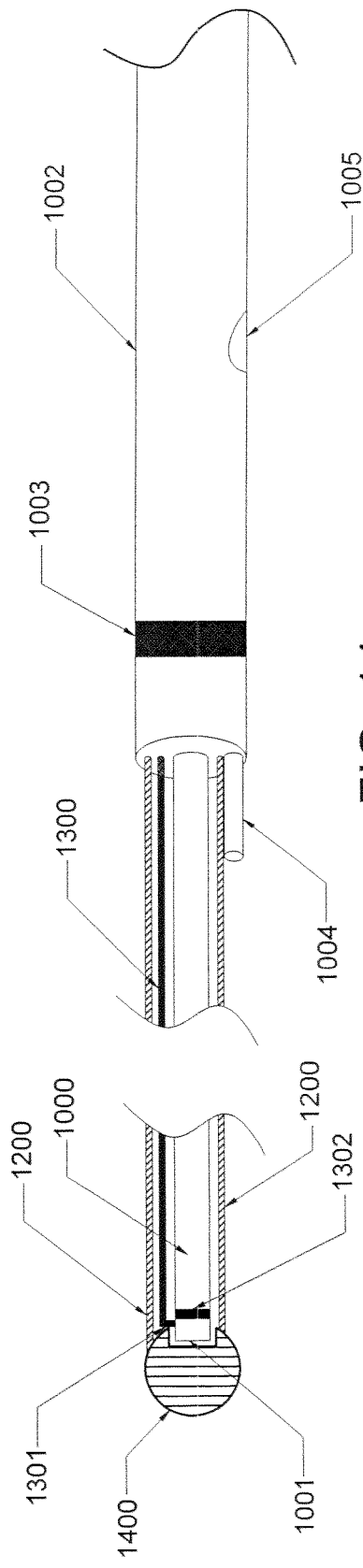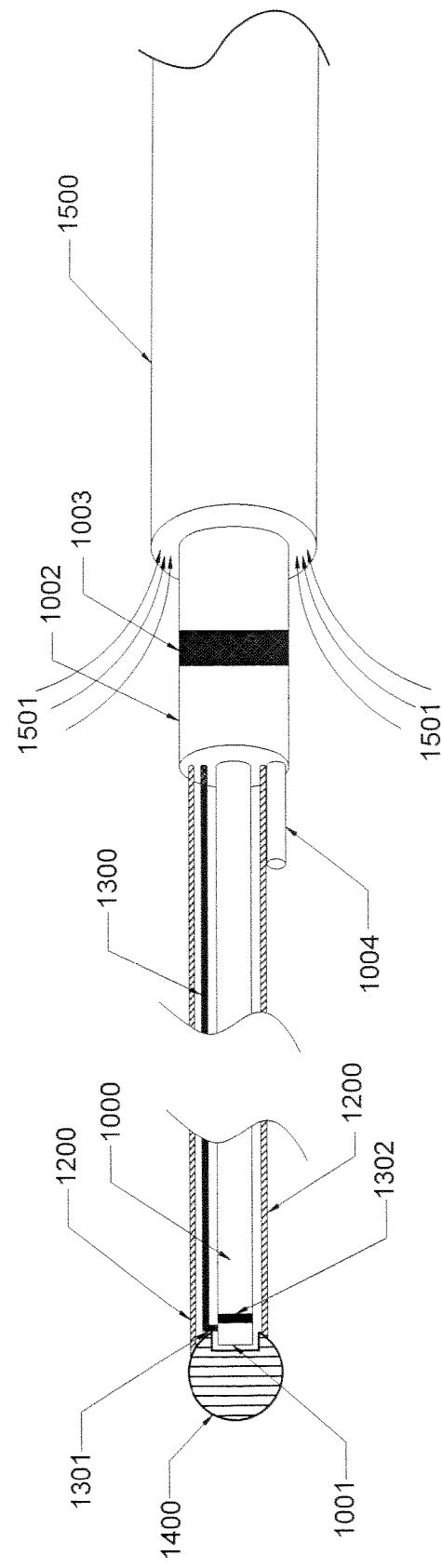

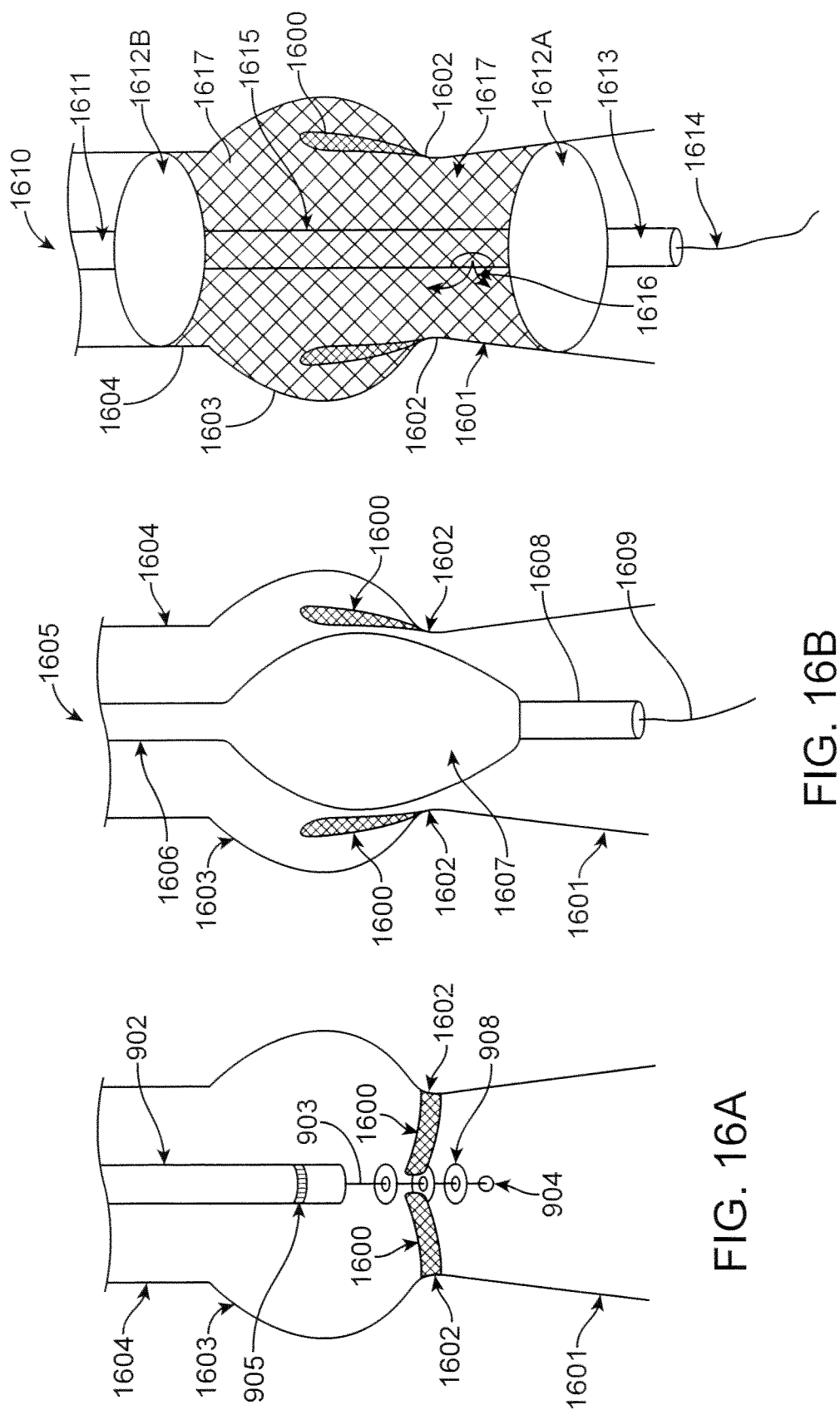

METHODS AND DEVICES FOR ENDOVASCULAR THERAPY

CROSS-REFERENCES TO RELATED APPLICATIONS

This application claims priority to US Provisional Application No. 61/278,353, of Wallace, filed on Oct. 6, 2009, and is a continuation-in-part of co-pending application Ser. No. 13/962,646 filled on Aug. 8, 2013, which is a continuation-in-part of co-pending application Ser. No. 13/625,405 filled on Sep. 24, 2012, which is a continuation-in-part of co-pending application Ser. No. 13/438,221 filled on Apr. 3, 2012, which is a continuation-in-part of co-pending application Ser. No. 13/134,470 filled on Jun. 8, 2011, which is a continuation-in-part of co-pending application Ser. No. 12/930,415 filed Jan. 6, 2011, which is a continuation-in-part of co-pending application Ser. No. 12/925,495 filed Oct. 22, 2010, which is a continuation-in-part of co-pending application Ser. No. 12/807,129, filed Aug. 27, 2010, which is in turn continuation-in-part of co-pending application Ser. No. 12/661,853, filed Mar. 25, 2010.

TECHNICAL FIELD OF THE INVENTION

The present invention is related to medical devices and methods. More specifically, the invention is related to endovascular devices and methods for the treatment of stenosis, inhibiting restenosis, plaque removal, thrombus removal, crossing totally occluded arteries or veins, the treatment of heart valves, and the treatment of vulnerable plaque and the removal of tissue, blood clots and liquids from the human body. Treatment of these diseases may be performed with or without the use of therapeutic drugs.

BACKGROUND

Atherosclerosis and its consequences, including arterial stenosis, venous stenosis and hypertension, represent a major health problem both in the U.S. and throughout the world. A common treatment for arterial stenosis and occlusions involves balloon angioplasty, more specifically percutaneous transluminal balloon angioplasty (PTA), a procedure in which a balloon catheter is advanced through the artery to the stenotic or occluded site and expanded there to widen the artery. A stent is also commonly placed at the stenotic site for the purpose of maintaining patency of the newly opened artery. Angioplasty and stent implantation, however, often are of limited long term effectiveness due to restenosis and reocclusion. In a study of intracoronary stenting, for example, restenosis was observed to occur over the long term in 15% to 30% of patients (Serruys et al., 1994, N. Engl. J. Med. 331: 489).

The use of therapeutic agents with presumed antistenotic or anti-intimal thickening activity has been combined with stent-based therapy. Drug-eluting stents that deliver a drug such as Sirolimus or Paclitaxel have been used most frequently in the hope that a slowly eluting drug will impede restenosis. In another recent approach, balloon catheters with drug eluting balloons have been tried for restenosis prevention. While these approaches have met with some success, the restenosis problem is far from solved, as drug eluting stents and balloons have had mixed results in clinical studies.

Yet another approach to treating vascular stenosis and preventing restenosis involves administering a therapeutic agent at the stenosis site, either alone or in conjunction with a conventional endovascular interventional procedure such as angioplasty or venoplasty, with or without stenting. In this approach a therapeutic agent is delivered to the stenotic site through a catheter. Numerous therapeutic agents have been examined for their anti-proliferative effects, and some of which have shown some effectiveness with regard to reducing intimal hyperplasia. These agents, by way of example, include heparin and heparin fragments, angiotensin converting enzyme (ACE) inhibitors, angiopeptin, cyclosporin A, goat-anti-rabbit PDGF antibody, terbinafine, trapidil, tranilast, interferon-gamma, rapamycin, corticosteroids, fusion toxins, antisense oligonucleotides, and gene vectors. Other non-chemical approaches have also been tried, such as ionizing radiation.

While holding considerable promise, the methods and devices for delivering antistenotic therapeutic agents to blood vessel wall tissue are as yet not fully satisfactory. Absorption of the therapeutic agent into the blood vessel wall, for example, represents a significant challenge. Furthermore, it would be advantageous to incorporate or coordinate delivery of a therapeutic with an angioplasty, venoplasty and/or stent placement procedure. Any attractive new methods or devices for therapeutic agent delivery would need to be safe, effective, and relatively simple to perform. At least some of these objectives are met by the embodiments of the invention as provided herein.

A need exists for devices and methods that allow ultrasound energy to be more evenly applied to the vessel wall, and to induce homogeneous cellular changes to increase vessel permeability, so that therapeutic drugs can be more effective. Ideally, such devices would provide sufficient delivery of ultrasound energy to the surrounding tissue (either to small or large vessels), and consequently increase vessel drug uptake. While such devices should provide necessary ultrasound energy, they also should avoid and prevent vascular injuries. Also, dissolving endovascular blood clots maybe more efficient when ultrasound energy is delivered uniformly to the treatment area. At least some of these objectives will be met by the present invention.

BRIEF SUMMARY OF THE INVENTION

The scope of the present invention is best defined by the appended claims. In certain instances, detailed descriptions of ultrasound physics, well-known devices, compositions, components, mechanisms and methods are omitted so as to not obscure the description of the present invention with unnecessary details.

The inventive technology described herein provides new methods and devices to improve the treatment of vascular stenosis and re-stenosis using ultrasound technology to enhance delivery of therapeutic agents directly to a targeted therapeutic site, such as a stenotic site on an arterial or vein wall. Aspects of the anti-stenotic treatment methodology may include ultrasound-enhanced delivery of therapeutic agents to a stenotic site to reduce plaque and to increase the patency of the afflicted vessel as stand-alone or first treatment options performed without other physical interventions directed toward increasing vessel patency, or such treatments may done in conjunction with other interventional approaches, such as treatment of a site previously treated or contemporaneously treated to inhibit or prevent re-stenosis.

Embodiments of the invention include a method and devices for treating stenosis or inhibiting restenosis in an artery or vein by delivering a therapeutic agent into the artery or vein and enhancing absorption of the therapeutic agent into a wall of the artery or vein using ultrasound energy. Such method includes advancing a distal end of a combined ultrasound/drug delivery catheter to an area of stenosis or restenosis in an artery or vein; delivering a stenosis inhibiting therapeutic agent into the artery or vein from the ultrasound/drug delivery catheter; and activating the ultrasound catheter to emit ultrasound energy while delivering the therapeutic agent.

Another embodiment of the present invention includes a method and devices for treating or inhibiting restenosis in an artery or vein by first delivering ultrasound energy to the vessel wall and exposing the vessel wall to ultrasound energy using an ultrasound catheter. After exposing the vessel wall to ultrasound energy, a stenosis inhibiting therapeutic agent is delivered into the artery or vein. Delivery of such a therapeutic agent can be accomplished with the same device or through a separate drug delivery catheter. A separate catheter to deliver therapeutic drug may be an ultrasound energy catheter or any other drug delivery catheter.

Alternatively, the present invention also includes a method and devices for treating or inhibiting restenosis in an artery or vein by delivering ultrasound energy from an external ultrasound energy source from outside of the body, through the skin (also known as transcutaneous approach). After exposing the vessel wall to ultrasound energy from the external source, a stenosis inhibiting therapeutic agent is delivered into the artery or vein. Delivery of such therapeutic agent can be accomplished by using an endovascular drug delivery catheter.

These methods and devices for treating stenosis or inhibiting restenosis are such that the delivery of the ultrasonic energy either from an external ultrasound energy source or from an endovascular ultrasound device causes vasodilatation within vessel wall. In typical embodiments of the method, the therapeutic agent is delivered from the ultrasound drug delivery catheter at or near the distal end, and activating the ultrasound drug delivery catheter converts the therapeutic agent into droplets.

In various embodiments, the therapeutic agent may be dispersed at a constant rate or a variable rate. In some embodiments, the therapeutic agent is delivered from a plurality of outlet ports that are arrayed around the distal end of the ultrasound catheter. In other embodiments, the therapeutic agent may be delivered from a perfusion porous balloon, a balloon coated with the therapeutic agent or from an expandable mesh coated with the therapeutic agent located at the distal end of the ultrasound drug delivery catheter. In still other embodiments, the therapeutic agent is delivered in radial fashion through at least one of the outlet ports located in the distal tip of the ultrasound drug delivery catheter or outlet ports located on the ultrasound catheter body proximal to the distal tip. In another embodiment, the therapeutic agent can be delivered following delivery of ultrasound energy to the vessel wall in any desirable fashion, utilizing the same or different ultrasound catheter or employing these methods using any conventional drug delivery catheter.

Some embodiments of the method and devices for treating stenosis or inhibiting restenosis further include delivering an irrigation fluid through the ultrasound catheter during the ultrasound catheter activation. In some of these embodiments, the irrigation fluid and the therapeutic agent are delivered together in a mixture; in other embodiments, the irrigation fluid is delivered separately from the therapeutic agent. In these latter embodiments, the method may include introducing an irrigation fluid via one or more outlet ports on the ultrasound/drug delivery catheter that are separate from one or more therapeutic agent outlet ports.

The scopes of the embodiments of the method and devices include the application of any therapeutic agent to a target site, such agents considered to be medically beneficial to the patient being treated, and examples of such agents are provided in the detailed description. The therapeutic agent or agents may be in any of the following forms; liquid, powder, particle, microbubbles, microspheres, nanospheres, liposomes and combinations thereof. The therapeutic agent(s) may be delivered directly to the treatment area in a solution-liquid form or can be placed on the surface of other devices, such as stents or balloons, and delivered to the treatment area.

Embodiments of the method and devices for treating stenosis or inhibiting restenosis may further include repositioning or moving the ultrasound drug delivery catheter during ultrasound energy activation and a therapeutic agent delivery to further enhance drug delivery.

Embodiments of the method and devices for treating stenosis or inhibiting restenosis may further include a blood flow protection device(s), such as balloon devices that are independent from ultrasound delivery device or coupled to the ultrasound catheter, within the artery or vein to prevent the therapeutic agent from flowing down stream. In such embodiments, expanding the blood flow protection device includes expanding it in at least one of the locations of distal to the ultrasound catheter distal tip or proximal to the ultrasound catheter distal tip. These method embodiments may further include removing the therapeutic drug trapped by the blood flow protection device(s) from the body.

Embodiments according to the present invention for treating stenosis or inhibiting restenosis may further include delivering therapeutic agent after the delivery of ultrasound energy: first exposing the treatment area to ultrasound energy either from an external ultrasound source (such as an ultrasound transducer) or from an endovascular ultrasound catheter, and after ultrasound, exposing to the vessel wall, arterially or venously delivering the therapeutic agent to the treatment area.

In some embodiments of the present invention for treating stenosis or inhibiting restenosis, advancing the ultrasound drug delivery catheter includes advancing it in a manner selected from monorail, over-the-wire, and without the use of a guide-wire. In various embodiments, the ultrasound catheter can operate in continuous mode, pulse mode and a combination continuous/pulse mode, and in some embodiments the ultrasound energy can be modulated. Modulation of ultrasound energy may include modulation of voltage, current, frequency or pulse parameters such as ultrasound energy ON/OFF time or any combination of all. In still other embodiments, advancing the ultrasound/drug delivery catheter may include contacting the wall of the blood vessel with the catheter.

Some embodiments of the present invention for treating stenosis or inhibiting restenosis further include performing an angioplasty or venoplasty procedure before, during or after delivery of the therapeutic agent and ultrasound energy, wherein the angioplasty or venoplasty procedure can be balloon angioplasty or venoplasty, stent placement, atherectomy, laser angioplasty or venoplasty, ultrasound angioplasty or venoplasty, cryoplasty, or a combination of these procedures. In various embodiments, performing the angioplasty or venoplasty procedure includes advancing a balloon device over a guidewire to the area of stenosis or restenosis in the artery or vein, wherein the combined ultrasound drug delivery catheter is advanced over the same guidewire.

In various other embodiments of the present invention, treating stenosis or inhibiting restenosis further include performing an angioplasty or venoplasty procedure before, during or after delivery of the ultrasound energy and delivery of therapeutic agent is performed separately from delivering ultrasound energy, either during or after delivering ultrasound energy.

In another aspect, the present invention provides a method for treating stenosis and inhibiting restenosis in an artery or vein by dilating the artery or vein, delivering a therapeutic agent to the artery or vein, and at the same time enhancing absorption of the therapeutic agent using ultrasound energy. In this aspect, the method may include advancing a distal portion of a combined dilation, ultrasound, drug delivery catheter to an area of stenosis or restenosis in an artery or vein; expanding an arterial dilator of the catheter to dilate the artery or vein at the area of stenosis or restenosis; delivering a stenosis inhibiting therapeutic agent into the artery or vein through the catheter; and activating the catheter to emit ultrasound energy while delivering the therapeutic agent In still another aspect, the present invention provides a method and devices for treating stenosis and inhibiting restenosis in an artery or vein by delivering a therapeutic agent to the artery or vein and enhancing absorption of the therapeutic agent using ultrasound energy. In this aspect, the method may include advancing a distal portion of a combined ultrasound/drug delivery catheter to an area of stenosis or restenosis in an artery or vein; expanding an expandable member, such as a balloon, coupled with the catheter at least one of distal or proximal to a drug delivery portion of the catheter, to prevent the therapeutic agent from flowing at least one of proximally or distally beyond the expandable member; delivering a stenosis inhibiting therapeutic agent into the artery or vein through the catheter; and activating the catheter to emit ultrasound energy while delivering the therapeutic agent. In various of these particular embodiments, expanding the expandable member includes expanding a member either distal to or proximal to the drug delivery portion of the catheter. In some embodiments, expanding the expandable member includes expanding two expandable members, one distal to and one proximal to the drug delivery portion of the catheter.

In still another aspect, the present invention provides a method and devices of treating vulnerable plaque that includes introducing an ultrasound dispersed therapeutic agent to a treatment area: and activating ultrasound energy to cause passage of the therapeutic drug into the vessel wall.

In still another aspect, the invention provides a method and devices for treating stenosis or inhibiting restenosis in a totally occluded artery or vein by delivering a therapeutic agent into the artery or vein and enhancing absorption of the therapeutic agent into a wall of the artery or vein using ultrasound energy. This embodiment may include advancing a distal end of a combined ultrasound/drug delivery catheter to an area of a totally occluded artery or vein; delivering a stenosis inhibiting therapeutic agent into the artery or vein from the ultrasound/drug delivery catheter; and activating the ultrasound catheter to emit ultrasound energy while delivering the therapeutic agent. In some of these embodiments, advancing a distal end of a combined ultrasound/drug delivery catheter to an area of stenosis or restenosis in an artery or vein is performed without ablation or removal of material. In other embodiments, treating stenosis or inhibiting restenosis in an artery or vain by delivering a therapeutic agent into the artery or vain and enhancing absorption of the therapeutic agent into a wall of the artery or vain using ultrasound energy further includes ablation or removal of material.

Embodiments of the inventive therapeutic methodology will now be summarized with reference to an approach to antistenotic treatment of blood vessels more broadly, whether the treatment site is being subjected to a first treatment, a repeat treatment following any other antistenotic treatment, a follow up treatment to prevent or inhibit restenosis following a previous antistenotic treatment of any kind, and whether the treatment site is totally occluded, partially occluded, experiencing in-stent occlusion, vein graft occlusion, or artificial graft occlusion, or diagnosed as being vulnerable to occlusion, or any combination thereof.

Embodiments of the inventive methods and devices provided herein relate to approaches to antistenotic treatment at a target site in a blood vessel, a vein or an artery, for example, by using ultrasound energy to enhance delivery of a therapeutic agent. The site of treatment may be a site that has not been previously treated, the treatment embodiment thereby being a first therapeutic intervention, or the treatment site may have been treated before by another interventional method, or even by the present inventive method (i.e., a repeat treatment). In some embodiments of the method, the ultrasound-enhanced therapeutic agent is applied in close temporal conjunction with other interventional methods, such as angioplasty or venoplasty. In various embodiments the method may be applied to vessels with a range of stenosis or plaque buildup, ranging from mild occlusion to total occlusion. In other embodiments, the method may be applied to treatment sites in order to impede or prevent restenosis following an earlier treatment. In still other embodiments, the method may be applied to sites identified as being vulnerable to stenotic processes. The scope of embodiments of the method includes the application of any therapeutic agent to a target site, such agents considered to be medically beneficial to the patient being treated.

Embodiments of the method and devices of antistenotic treatment include positioning a distal end of a combined ultrasound drug delivery catheter proximate the treatment site in a blood vessel. This positioning of the catheter proximate the site may be accomplished without ablating or removing any plaque material that may be present. Embodiments of the method further include delivering a fluid formulation including a therapeutic agent to the site from the ultrasound drug delivery catheter; and emitting ultrasound energy from the ultrasound catheter while delivering the therapeutic agent. In some embodiments of the method, a dilator may also be positioned at the treatment site and dilated, such dilation increasing the efficiency and consistency of ultrasound delivery to areas of the internal vessel surface at the treatment site. While, as noted above, some embodiments of the method do not include direct physical or energy delivery attack on plaque, other embodiments may include ablating, removing, or compressing plaque material at the treatment site.

With regard to aspects of the delivery of ultrasound energy to the target site, the ultrasound energy source (such as an external ultrasound transducer or endovascular ultrasound catheter or ultrasound drug delivery catheter) may be operated in a continuous mode, a pulse mode, or in any combination or sequence thereof; further the ultrasound energy may be modulated. In general, the emitted ultrasonic energy is sufficient to cause vasodilatation of the blood vessel and/or sonoporation within cells of the vessel wall proximate the target site, preferably, without causing vascular damage. Alternatively, ultrasound energy may be delivered separately from delivering therapeutic agent using the same device or a different device. A different conventional drug delivery catheter may be used together with ultrasound delivery catheter.

As noted above, some embodiments may include repeated applications, or multiple applications at the same site, or at another portion of a larger treatment site. Thus, for example, embodiments of the method may include repositioning the ultrasound drug delivery catheter; and repeating the step of emitting ultrasonic energy. Positioning the ultrasound drug delivery catheter at the target site may include positioning the catheter nearby the target site, or it may include contacting the vessel wall at the site. In some embodiments, the contacting may be optimized by dilation of the treatment site, so as to optimize and make uniform a therapeutically effective contact between the ultrasound catheter and the target tissue.

Some embodiments include advancing an ultrasound/drug delivery catheter to the treatment site either prior to or in conjunction with appropriate positioning of the catheter for treatment of the site. Advancing the catheter may be accomplished by conventional approaches either with or without a guidewire. Guidewire-assisted methods may include any approach, such as over-the-wire, or monorail deployment.

Some embodiments of the method and devices of antistenotic treatment may further include expanding a first blood flow prevention member coupled to the catheter at a site proximate the drug delivery portion of the catheter to a degree of expansion sufficient to prevent the therapeutic agent from flowing in the vessel beyond the expandable member. In these embodiments, a blood flow protection member, such as a balloon, may be disposed distal to (typically, downstream from) a drug delivery portion of the catheter. In other embodiments, a blood flow protection member may be disposed proximal to (typically, upstream from) a drug delivery portion of the catheter. In still other embodiments, two blood flow protection members may be disposed proximate the drug delivery portion of the catheter, one member disposed distally, the other disposed proximally. In some embodiments of the method that make use of blood flow prevention members in order to contain released drug into a confined vascular space, the method may further include removing such trapped drug from the body after the ultrasonic treatment, and before collapsing the blood flow prevention members, allowing free flow of blood through the treated portion of the vessel. In yet another embodiment, therapeutic agent may be delivered to the vessel wall in conjunction with delivering ultrasound energy or separately after exposing the treatment area to ultrasound energy.

With regard to the formulation that includes the therapeutic agent that is being delivered by embodiments of the method, such formulation is typically in the form of a liquid, either aqueous, organic, or a combination thereof, such as an emulsion. Formulations may further include dispersions of powders or particles, microbubbles, microspheres, nanospheres, liposomes, or any combination thereof. The emitted ultrasound energy, per embodiments of the method, is sufficient to convert the formulation including the therapeutic agent into droplets, microdroplets, or aerosols. The therapeutic agent within its formulation may be dispersed from a drug delivery portion of the catheter at a constant or a variable rate, or any combination thereof.

Embodiments of the method and devices provided herein may further include holding the formulation with the therapeutic agent in a reservoir associated with the ultrasound/drug delivery catheter prior to the delivery step. These embodiments may include delivering the therapeutic agent formulation through one or more outlet ports in communication with the reservoir. In some embodiments, the reservoir may include a balloon, a stent or a mesh upon which the therapeutic agent is coated, and from which the agent is released or eluted.

Some embodiments of the method and devices provided herein further include delivering an irrigation fluid from the ultrasound catheter while emitting ultrasound energy. In some of these embodiments, the irrigation fluid and the therapeutic agent formulation are delivered together in a common mixture; in other embodiments, the irrigation fluid and the formulation including the therapeutic agent are delivered as separate fluids. When delivered separately, the irrigation fluid and the therapeutic agent formulation may be delivered from separate respective outlet ports.

Some embodiments of the method and devices further include performing an angioplasty procedure before, during or after delivery of the therapeutic agent and ultrasound energy, as summarized above. The angioplasty or venoplasty procedure may be of any conventional type, such as balloon device, stent placement, atherectomy, laser angioplasty or venoplasty, ultrasound angioplasty or venoplasty, cryoplasty, or any combination of such procedures. In some embodiments of this method, performing the angioplasty or venoplasty procedure may include advancing a balloon device over a guidewire to the target site, wherein the combined ultrasound/drug delivery catheter is advanced over the same guidewire.

Thus, one aspect of the invention includes an antistenotic treatment at a target site in a blood vessel that includes positioning a distal end of a combined ultrasound/drug delivery catheter to the site, delivering a fluid formulation including a therapeutic agent to the site from the ultrasound/drug delivery catheter, and emitting ultrasound energy from the ultrasound catheter while delivering the therapeutic agent, and performing an angioplasty or venoplasty procedure at the target site.

Another aspect of the invention includes an antistenotic treatment at a target site in a blood vessel that includes positioning a distal end of a combined ultrasound/drug delivery catheter to the site, emitting ultrasound energy from the ultrasound catheter without delivering the therapeutic agent, and then delivering a therapeutic agent to the site from the ultrasound/drug delivery catheter after first delivering ultrasound energy to the vessel wall.

In another aspect, the invention provides a method and devices for treating stenosis or inhibiting restenosis which includes emitting ultrasound energy from an ultrasound energy source and delivering a therapeutic agent intravenously into the human body.

In still another aspect, the invention provides a method and devices for treating stenosis or inhibiting restenosis which includes emitting ultrasound energy from an ultrasound energy source and delivering a therapeutic agent together with a contrast agent (either 100% or diluted with a conventional saline NaCl solution) into the artery or vein to the treatment location.

In still another aspect, the invention provides a method and devices for treating stenosis or inhibiting restenosis which includes emitting ultrasound energy from an ultrasound energy source and delivering at therapeutic agent in solution with Carbamide (an organic compound with the chemical formula $(NH_2)_2CO$) into the artery or vein to the treatment location.

In yet another aspect, the invention provides a method and devices for treating stenosis or inhibiting restenosis which includes emitting ultrasound energy from an ultrasound energy source and delivering a therapeutic agent with Drug Eluting Stents, Bioabsorbable Stents, Drug Eluting Balloons, Drug Eluting Stents, Porous Balloons, or Multi-Balloons to a treatment location that may include, but is not limited to, the artery, vein or heart valve. Multi-balloon drug delivery is also known as Weeping Balloons drug delivery, and includes an inflatable inner balloon enclosed by an expandable outer balloon that has holes. The annular space between the inner balloon and the outer balloon is configured to promote delivery of the fluid evenly through holes in the outer balloon to avoid problems of underloading and or overloading. The inner balloon may have various configurations including being tapered relative to the outer balloon. The outer balloon may also be tapered accordingly.

The scope of the embodiments and methods described herein include the application of any therapeutic agent to a target site for a period of time that is considered to be medically beneficial to the patient being treated. Any therapeutic drug may be exposed to the vessel for about one second to one hour to assure a maximum benefit of the delivered drug.

Suitable therapeutic agent(s) maybe delivered to the treatment area in variety of different forms and mixtures, either with or without ultrasound, and with or without interventional procedure.

Some embodiments of the method and devices of antistenotic treatment may further include removal of the therapeutic drug outside of the body, to avoid adverse systemic effects that may be caused by the therapeutic drug.

All these methods and devices for treating stenosis or inhibiting restenosis in an artery or vein by enhancing permeability of the vessel wall using ultrasound energy and delivering a therapeutic agent into the artery or vein may be achieved with endovascular or transcutaneous techniques of delivery ultrasound energy. The therapeutic drug may be delivered to the treatment site before, during and after ultrasound energy delivery.

Vascular permeability, often in the form of capillary permeability or microvascular permeability, characterizes the capacity of a blood vessel wall to allow for the flow of small molecules or even whole cells in and out of the vessel. Blood vessel walls are lined by a single layer of endothelial cells. The gaps between endothelial cells (cell junctions) are strictly regulated depending on the type and physiological state of the tissue. The mechanical effect of ultrasound can disrupt this barrier by causing transcytosis, fenestration, channel formation, and/or opening of tight junction, thereby providing a free passage across the vascular wall to enhance delivery of therapeutic drugs.

Some other embodiments of the present invention include devices capable to further improve vessel permeability utilizing ultrasound energy propagated along a flexible member in the form of longitudinal waves, surface (radial or elliptic) waves and shear (transverse) waves, among other waves, simultaneously.

Other embodiments of the present invention include devices and methods utilizing ultrasound energy propagated in the form of longitudinal waves, surface (radial or elliptic) waves and shear (transverse) waves (among other waves) to change compliance of plaque or vessel obstruction, and to increase vessel permeability.

Resistant fibrotic plaque or calcified plaque is a major limitation in treating arterial disease. Calcium deposits are frequent in patients with advanced age, diabetes, renal insufficiency, hypertension, and a history of smoking. Calcified lesions are challenging to treat with traditional endovascular therapy such as conventional angioplasty. Frequently, to displace the calcified plaque, balloon inflation pressures of more than 20 atm is required. Even after calcific plaque is disposed, and the vessel is open, it still continues to be a significant barrier for the delivery of therapeutic drug to the vessel wall to further reduce stenosis and inhibit restenosis. Ultrasound energy can erode and fracture calcified plaque while causing minimal injury to a healthy tissue. Application of ultrasound longitudinal waves, surface (radial or elliptic) waves and shear (transverse) waves may induce micro-cracks in the plaque and create micro-channels to further facilitate therapeutic drug penetration and permeability of the vessel.

In another embodiment, the invention provides devices and methods for ablating plaque, crossing Chronic Total Occlusions (CTO), as well as dissolving and removing blood clots and thrombus. This embodiment may include advancing a distal end of an ultrasound delivery device into the vessel, vein or other locations where plaque or blood clots are located, activating the ultrasound catheter to emit radial ultrasound energy, and applying aspiration or gravitational approach to further dissolve and remove blood clots outside the patient body. Use of therapeutic drug and/or microbubbles may enhance plaque and blood clots dissolving and removal process.

In patients undergoing endovascular procedures involving a vascular obstruction removal or administration of therapeutic drugs, use of ultrasound energy may be beneficial in the delivery of liquid medicament to further facilitate the distribution, delivery, absorption and/or efficacy of the medicament to improve clinical outcomes. Various ultrasonic catheter devices have been developed for use in ablating or otherwise removing obstructive material from blood vessels. For example, ultrasound devices with flexible ultrasound members for tissue ablation (either with or without therapeutic drugs) have been discussed in the prior art. Known devices enable translation of vibrations from the transducer to the flexible probe causing the probe to oscillate longitudinally or transversely. Longitudinal vibratory movement of the distal head or probe causes disintegration and ablation of the adjacent lesion while simultaneously delivering therapeutic drugs. Examples of such devices include U.S. Pat. Nos. 6,689, 086 and 6,929,632 (both by Nita, et al). Other examples of devices utilizing longitudinal vibrations are described in U.S. Pat. Nos. 6,855,123; 6,942,677; 7,137,963; 7,297,131; 7,393, 338; 7,621,929; 7,955,293; 8,133,236 and US Publication No. 2008/0108937 (all by Nita, et al.). Unlike longitudinal vibrations, transverse vibration emits a transverse ultrasonic energy along the length of the probe body so that a plurality of transverse nodes and anti-nodes are formed along the length of the probe. Examples of such devices include U.S. Pat. Nos. 6,524,251; 6,551,337; 6,652,547; 6,660,013; 6,695.781; 6,733,451; 6,866,670; 7,494,468; and 7,503,896 (all by Rabiner, et al.). While the longitudinal waves oscillate in the longitudinal direction or the direction of wave propagation, transverse waves oscillate perpendicular to the direction of propagation. Transverse waves are relatively weak compared to longitudinal waves and are known to not effectively propagate through liquids. Also, transverse vibrations are known to produce unwanted stress along the ultrasound transmission member, often causing breakage of the ultrasound transmission member. While longitudinal waves (as described in the prior art) are powerful, their ability to deliver ultrasound energy to the surrounding vessel wall is limited to the vibrating tip area. Therefore, longitudinal and transverse vibrations are limited in inducing uniform cellular changes along the treated vessel wall to further facilitate drug therapies.

The present invention provides methods and devices configured to deliver ultrasound surface waves or radial vibrational energy along an ultrasound transmission member to the surrounding tissue, to either small or large vessels or other cavities, and consequently increasing vessel drug uptake. Such devices provide a desired level of ultrasound energy to induce cellular changes while preventing vascular damage and reducing the potential of breakage for the ultrasound transmission member.

The present invention also provides methods and devices configured to deliver ultrasound energy and ultrasound enhanced delivery of Paclitaxel for heart valve therapies. There are four valves in the heart: the aortic valve, pulmonary valve, mitral valve, and tricuspid valve; each at the exit of one of the heart's four chambers. Heart valve stenosis/restenosis is a common valve disease. Balloon valvuloplasty is used primarily to treat heart valves when narrowing is present and medical treatment has not corrected or relieved the related problems. During a balloon valvoplasty, a specially designed balloon catheter is inserted into a blood vessel in the groin and guided to the heart. The tip of the catheter is directed inside the narrowed valve, and the balloon is inflated and deflated several times to widen the valve opening. Once the valve has been widened enough, the balloon catheter is removed.

Calcification of heart valves, also known as calcific degeneration, occurs when calcium builds up on a heart valve. This makes the leaflets of the valve harder and thicker and causes them to work less efficiently. If the calcium build-up on a valve is severe enough, the valve will no longer function properly, causing the valve to leak. All four valves of the heart can become calcified, but the aortic valve is the most common site of calcification. While valvular angioplasty often offers relief and cures the problem, calcification of heart valves requires surgery to remove calcium from leaflets to correct the opening (surgical valvotomy). Frequently, a valve replacement is necessary. Valvuloplasty and valvotomy play a very important role in valve deployment. Therefore, a need for less invasive methods to treat valvular stenosis/restenosis and calcifications still exists.

BRIEF DESCRIPTION OF THE DRAWINGS

FIGS. 2A, 2B, and 2C show various views of embodiments of ultrasound catheters for delivering a therapeutic agent to inhibit stenosis.

FIG. 2A shows a side view of an ultrasound-enhanced drug delivery catheter.

FIG. 2B shows a view of a longitudinal cross section of an embodiment of an ultrasound-enhanced drug delivery catheter.

FIG. 2C shows a view of a longitudinal cross section of an alternative embodiment of an ultrasound-enhanced drug delivery catheter.

FIGS. 3A, 3B, and 3C show side views of embodiments of an ultrasound-enhanced drug delivery catheter at a stenosis therapy site.

FIG. 3A shows an embodiment of the ultrasound catheter with holes at the distal tip of the catheter for the delivery of a therapeutic agent.

FIG. 3B shows an embodiment of an ultrasound catheter with ports in the wall of the catheter body for the delivery of a therapeutic agent.

FIG. 3C shows an embodiment of an ultrasound catheter with therapeutic agent delivery sites in the form of holes at the distal tip of the catheter and delivery ports in the wall of the catheter body.

FIG. 4B shows an embodiment of the ultrasound-enhanced drug delivery catheter delivering therapeutic agent to a stenotic site following a balloon angioplasty or venoplasty procedure.

FIG. 5 shows an embodiment of an ultrasound-enhanced drug delivery catheter delivering therapeutic agent to a stenotic site, the catheter further associated with an expanded distal protection balloon device positioned at the distal end of a guidewire, the expanded balloon filling the vessel lumen and preventing downstream the flow of therapeutic agent.

FIG. 7A shows an embodiment of an ultrasound-enhanced drug delivery catheter emitting ultrasound energy to the vessel wall first.

FIG. 7B shows an embodiment of an ultrasound-enhanced drug delivery catheter delivery therapeutic agent after delivering ultrasound energy.

FIGS. 12-15 show different embodiments of the distal ultrasound transmission member shown in FIG. 10.

FIG. 16A illustrates a side view of an ultrasound catheter positioned within a heart valve.

FIG. 16B illustrates a side view of single-balloon valvuloplasty using an ultrasound catheter according to another embodiment of the present invention.

FIG. 16C illustrates a side view of a therapeutic drug delivery according to another embodiment of the present invention.

DETAILED DESCRIPTION OF THE INVENTION

Figure 1:
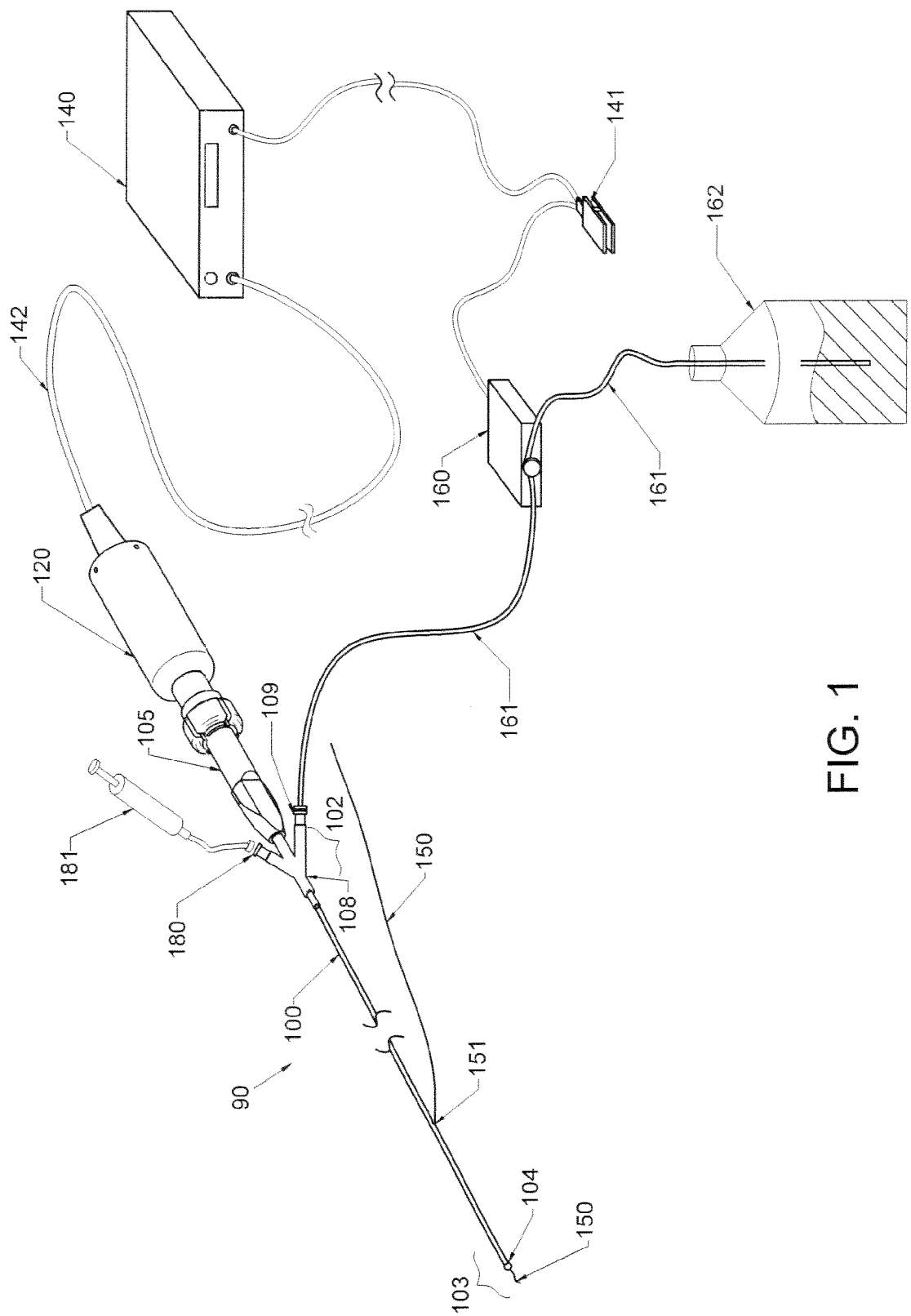
FIG. 1 shows arm embodiment of an ultrasound-enhanced drug delivery system.

The present application provides new methods and devices to improve the treatment of vascular stenosis and re-stenosis using ultrasound technology to enhance delivery of therapeutic agents directly to a targeted therapeutic site, such as a stenotic site on an artery or vein wall. These methods may be understood as forms of anti-stenosis treatment, which may include treatment of a stenotic site to modify plaque compliance and to increase the patency of the afflicted vessel, or it may also include treatment of a site previously treated or contemporaneously treated to inhibit or prevent restenosis. Aspects of the invention, including devices and the types of therapeutic agents whose efficacy may be enhanced by the provided technology will be described first in general terms, and then, further below, will be described in the context of FIGS. 1-16.

The methods described herein employ endovascular sonophoresis and induce vasodilatation, a process that creates micro-indentations in a vessel wall during ultrasound energy delivery; these indentations increase vessel wall permeability and permit a higher level of therapeutic agent delivery to the target cell interior. When ultrasound energy is delivered at a frequency range of 1 kHz-10 MHz and at power below 20 watts to the vessel wall, the sound waves transiently disrupt the integrity of the plaque and the cell membranes without creating permanent damage to the vessel wall or surrounding tissue. In a typical embodiment of the invention, for example, ultrasound energy from a source in contact or in proximity to a vessel wall, at a frequency of about 20 kHz and a power of less than about 10 watts is used to induce sonoporation and vasodilatation by creating micro-cracks and micro-channels in the plaque, and to modify the integrity of cell membranes. Power levels above 20 watts may cause permanent damage to the vessel wall such as thermal damage, necrosis and vessel rupture when ultrasound energy is delivered by an endovascular catheter. Power levels above 20 watts may also cause skin burns or wounds when ultrasound energy is delivered transcutaneously through the skin.

As used herein, "power" of the endovascular catheter delivering ultrasound energy refers to watts of power delivered by the distal end or tip of the catheter per $mm^2$ of the tip's or distal end's cross-sectional area. For transcutaneous delivery of ultrasound energy, "power" refers to a total amount of watts of power of the ultrasound device per cm of the contact area between the device and the skin.

Sonoporation uses the interaction of ultrasound energy with the presence of locally or systemically delivered drugs to temporarily permeabilize the cell membrane allowing for the uptake of DNA, drugs, and other therapeutic compounds from the extracellular environment. This membrane alteration is transient, leaving the compound trapped inside the cell after ultrasound exposure. Sonoporation combines the capability of enhancing gene and drug transfer with the possibility of restricting this effect to the desired area and the desired time. Thus, sonoporation is a promising drug delivery and gene therapy technique, limited only by a full understanding regarding the biophysical mechanism that results in the cell membrane permeability change.

Oscillation of delivered therapeutic agents is considered to be a primary mechanism causing sonoporation. However, inertial cavitation, microstreaming, shear stresses, and liquid jets as a result of linear and nonlinear oscillations all may be causal mechanisms contributing to sonoporation as well. Propagating ultrasound pressure waves have an impact in regulating endothelial cell function, cell morphology, metabolism, and gene expression. Fluid shear stress caused by propagating ultrasound waves induces a rapid, large, and sustained increase in Nitric Oxide activity. In the very acute setting (seconds) of shear stress, calcium-activated potassium channels open and increase Nitric Oxide production. Nitric Oxide contributes to vessel dilation by inhibiting vascular smooth muscle constriction. This Nitric Oxide delivery may improve targeted therapeutic delivery into vascular tissues.

In some embodiments of the invention, the method and devices may include converting a therapeutic agent from liquid form into spray via ultrasound, a method known as nebulization that converts the low viscosity drug into an ultra fine spray as it exits from the catheter tip. Thus, this allows a rapid cellular uptake of drug and enables it to easily pass through the hydrophobic barrier of cell membranes. As the drug is delivered through the catheter, it is mechanically pulverized into droplets from the vibrating distal end of the catheter, further increasing permeation of the drug into the vessel wall.

In one aspect, methods and improved devices are provided for inhibiting stenosis, restenosis, and/or hyperplasia concurrently with and/or after intravascular intervention. As used herein, the term "inhibiting" means any one of reducing, treating, minimizing, containing, preventing, curbing, eliminating, holding back, or restraining. In some embodiments, ultrasound enhanced delivery of therapeutic agents to a vessel wall with increased efficiency and/or efficacy is used to inhibit stenosis or restenosis. Such a method may also minimize drug washout and provide minimal to no hindrance to endothelialization of the vessel wall.

As used herein, "treatment site" refers to an area in a blood vessel or elsewhere in the body that has been or is to be treated by methods or devices of the present invention. Although "treatment site" will often be used to refer to an area of a vessel wall that has stenosis or restenosis ("a stenotic site"), the treatment site is not limited to vascular tissue or to a site of stenosis. The term "intravascular intervention" includes a variety of corrective procedures that may be performed to at least partially resolve a stenotic, restenotic, or thrombotic condition in a blood vessel, usually an artery or vein of a human body. Commonly, at least in current practice, the therapeutic procedure may also include balloon angioplasty or venoplasty. The corrective procedure may also include directional atherectomy, rotational atherectomy, laser angioplasty or venoplasty, stenting, or the like, where the lumen of the treated blood vessel is enlarged to at least partially alleviate a stenotic condition which existed prior to the treatment. The treatment site may include tissues associated with endovascular locations, or outside of endovascular location, including bodily lumens, organs, ducts or localized tumors. In one embodiment, the present devices and methods reduce the formation or progression of restenosis and/or hyperplasia that may follow an intravascular intervention. A "lumen" may be any blood vessel in the patient's vasculature, including veins, arteries, aorta, heart valves and particularly including coronary and peripheral arteries, as well as previously implanted grafts, shunts, fistulas and the like. In alternative embodiments, methods and devices described herein may also be applied to other body lumens, such as the biliary duct, which are subject to excessive neoplastic cell growth. Examples of internal corporeal tissue and organ applications include various organs, head, nerves, glands, ducts, and the like.

As used herein, "therapeutic agent" includes any molecular species, and/or biologic agent that is either therapeutic as it is introduced to the subject under treatment, becomes therapeutic after being introduced to the subject under treatment, for example by way of reaction with a native or non-native substance or condition, or any other introduced substance. Examples of native conditions include pH (e.g. acidity), chemicals, temperature, salinity, osmolality, and conductivity; with non-native conditions including those such as magnetic fields, electromagnetic fields (such as radiofrequency and microwave), and ultrasound. In the present application, the chemical name of any of the therapeutic agents is used to refer to the compound itself and to pro-drugs (precursor substances that are converted into an active form of the compound in the body), and/or pharmaceutical derivatives, analogues, or metabolites thereof (bio-active compound to which the compound converts within the body directly or upon introduction of other agents or conditions (e.g., enzymatic, chemical, energy), or environment (e.g. pH).

The scope of the invention includes the use of any therapeutic agent whose medicinal effectiveness may be enhanced by the use of ultrasonic energy, as described herein. For the purposes of illustration, a number of therapeutic agent classes will be identified in order to convey an understanding the invention. These classes of agents and the specific listed agents are not intended to limit the scope or practice of the invention in any way; the scope of the invention includes any therapeutic agent that may be considered beneficial in the treatment of a patient. Further, these agents may be delivered by any appropriate modality, as for example, by intra-arterial direct injection, intravenously, orally, or a combination thereof.

In some embodiments, examples of therapeutic agents may include immuno-suppressants, anti-inflammatories, anti-proliferatives, anti-migratory agents, anti-fibrotic agents, proapoptotics, vasodilators, calcium channel blockers, antineoplastics, anti-cancer agents, antibodies, anti-thrombotic agents, anti-platelet agents, IIb/IIIa agents, antiviral agents, mTOR (mammalian target of rapamycin) inhibitors, non-immunosuppressant agents, and combinations thereof.

Specific examples of therapeutic agents that may be used in various embodiments include, but are not limited to; mycophenolic acid, mycophenolic acid derivatives (e.g., 2-methoxymethyl derivative and 2-methyl derivative), VX-148, VX-944, mycophenolate mofetil, mizoribine, methylprednisolone dexamethasone, CERTICAN™ (e.g., everolimus, RAD), rapamycin, ABT-773 (Abbot Labs), ABT-797 (Abbot Labs). TRIPTOLIDE™, METHOTREXATE™, phenylalkylamines (e.g., verapamil), benzothiazepines (e.g., diltiazem), 1,4-dihydropyridines (e.g., benidipine, nifedipine, nicarrdipine, isradipine, felodipine, amlodipine, nilvadipine, nisoldipine, manidipine, nitrendipine, barnidipine (HYPOCA™)). ASCOMYCIN™ WORTMANNIN™ LY294002, CAMPTOTHECIN™, flavopiridol, isoquinoline, HA-1077 (1-(5-isoquinolinesulfonvyl)-homopiperazine hydrochloride). TAS-301 (3-bis(4-methoxyphenyl)methylene-2-indolinone), TOPOTECAN™ hydroxyurea, TACROLIMUS™ (FR 506), cyclophosphamide, cyclosporine, daclizumab, azathioprine, prednisone, diferuloymethane, diferuloylmethane, diferulylmethane, GEMCITABINE™, cilostazol (PLETAL™), tranilast, enalapril, quercetin, suramin, estradiol, cycloheximide, tiazofurin, zafurin, AP23573, rapamycin derivatives, non-immunosuppressive analogues of rapamycin (e.g. rapalog. AP21967, derivatives' of rapalog), CCI-779 (an analogue of rapamycin available from Wyeth), sodium mycophernolic acid, benidipine hydrochloride, sirolimus, rapamine, metabolites, derivatives, and or combinations thereof.

In some embodiments, the method and devices may include introducing anti-cancer therapeutic agents for promoting intracellular activation by irradiating the vessel wall cells with ultrasound to cause passage of the these drug into the vessel wall to inhibit stenosis and restenosis. In some embodiments, for example, an anti-angiogenesis agent may be used to inhibit stenosis or restenosis.

Ultrasound enhancement provided by the apparatus and method and devices of the present invention may be of particular benefit when the therapeutic agent being administered is highly toxic. Specific examples of such drugs are the anthracycline antibiotics such as adriamycin and daunorubricin. The beneficial effects of these drugs relate to their nucleotide base intercalation and cell membrane lipid binding activities. This class of drugs has dose limiting toxicities due to undesirable effects, such as bone marrow suppression, and cardiotoxicity.

Drugs within the scope of the present invention also include; Adriamycin PFS Injection (Pharmacia & Upjohn); Adriamycin RDF for Injection (Pharmacia & Upjohn); Alkeran for Injection (Glaxo Wellcome Oncology/HIV); Aredia for Injection (Novartis); BiCNU (Bristol-Myers Squibb Oncology/Immunology); Blenoxane (Bristol-Myers Squibb Oncology/-Immunology); Camptosar Injection (Pharmacia & Upjohn); Celestone Soluspan Suspension (Schering); Cerubidine for Injection (Bedford); Cosmegen for Injection (Merck); Cytoxan for Injection (Bristol-Myers Squibb Oncology/Immunology); DaunoXome (NeXstar); Depo-Provera Sterile Aqueous Suspension (Pharmacia & Upjohn); Didronel I.V. Infusion (MGI); Doxil Injection (Sequus); Doxorubicin Hydrochloride for Injection. USP (Astra); Doxorubicin Hydrochloride Injection. USP (ASTRA); DTIC-Dome (Bayer); Elspar (Merck); Epogen for Injection (Amgen); Ethyol for Injection (Alza); Etopophos for Injection (Bristol-Myers Squibb Oncology/Immunology); Etoposide Injection (Astra); Fludara for Injection (Berlex); Fluorouracil Injection (Roche Laboratories); Gemzar for Injection (Lilly); Hycamtin for Injection (SmithKline Beecham); Idamvcin for Injection (Pharmacia & Upjohn); Ifex for Injection (Bristol-Myers Squibb Oncology/Immunology); Intron A for Injection (Schering); Kytril Injection (SmithKline Beecham); Leucovorin Calcium for Injection (Immunex); Leucovorin Calcium for Injection. Wellcovorin Brand (Glaxo Welcome Oncology/HIV); Leukine (Immunex); Leustatin Injection (Ortho Biotech); Lupron Injection (Tap); Mesnex Injection (Bristol-Myers Squibb Oncology/Immunology); Methotrexate Sodium Tablets, Injection, for Injection and LPF Injection (Immunex); Mithracin for Intravenous Use (Bayer); Mustargen for Injection (Bristol-Myers Squibb Oncology/Immunology); Mutamycin for Injection (Bristol-Myers Squibb Oncology/-Immunology); Navelbine Injection (Glaxo Wellcome Oncology/HIV); Neupogen for Injection (Amgen); Nipent for Injection (SuperGen); Novantrone for Injection (Immunex); Oncaspar (Rhone-Poulenc Rorer); Oncovin Solution Vials & Hyporets (Lilly); Paraplatin for Injection (Bristol-Myers Squibb Oncology/Immunology); Photofrin for Injection (Sanofi); Platinol for Injection (Bristol-Myers Squibb Oncology/Immunology); Platinol-AQ Injection (Bristol-Myers Squibb Oncology/Immunology); Procrit for Injection (Ortho Biotech); Proleukin for Injection (Chiron Therapeutics); Roferon-A Injection (Roche Laboratories); Rubex for Injection (Bristol-Myers Squibb Oncology/Immunology); Sandostatin Injection (Novartis); Sterile FUDR (Roche Laboratories); Paclitaxel-Taxol Injection (Bristol-Myers Squibb Oncology/Immunology); Taxol Abraxane-ABI-007 (Abraxis Bioscience); Taxotere for Injection Concentrate (Rhone-Pou enc Rorer); TheraCys BCG Live (Intravesical) (Pasteur Merieux Connaught); Thioplex for Injection (Immunex); Tice BCG Vaccine, USP (Organon); Velban Vials (Lilly); Vumon for Injection (Bristol-Myers Squibb Oncology/Immunology); Zinecard for Injection (Pharmnacia & Upjohn); Zofran Injection (Glaxo Wellcome Oncology/HIV); Zofran Injection Premixed (Glaxo Wellcome Oncology/HIV); Zoladex (Zeneca).

Other classes of drugs within the scope of the present invention include alkylating agents which target DNA and are cvtoxic, nutagenic, and carcinogenic. All alkylating agents produce alkylation through the formation of intermediate. Alkylating agents impair cell function by transferring alkyl groups to amino, cartoryl, sulfhydryl, or phosphate groups of biologically important molecules. Such drugs include Busulfan (Myleran), Chlorambucil (Leukeran), Cyclophosphamide (Cytoxan, Neosor, Endoxus). Ifosfamide (Isophosphamide, Ifex), Melplihalan (Alkeran, Phenylalanine Mustargen, L-Pam, L-Sarcolysin), Nitrogen Mustargen (Mechlorethamine, Mustargen, HIV.sub.2). Nitrosonceas (Carmustine CBCNV, Bischlorethyl, Nitrosourea), Lomustine (CCNV, Cyclohexyl Chlorethyl Nitrosouren, CeeNV), semustine (methyl-CCNV) and Streptozocin (Strephozotocin), Streptozocin (Streptozoticin, Zanosan), Thiotepa (Theo-TEPA, and Triethylenethrophosphoranide).

Agents with alkylator activity include a group of compounds that include heavy metal alkylators (platinum complexes) that act predominantly by covalent bonding and "non-classic alkylating agents" are also within the scope of the present invention. Such agents typically contain a chloromethyl groups and an important N-methyl group. Such other agents include Amsacrine (m-AMSA, msa, Acridinylanisidiale, 4'-)(9-acridinylamins) methanesulfin-m-anesidide, Carboplatin (Paraplatin, Carboplatinum, CBDCA), Cisplatin (Cesplatinum), Dacabazine (DTIC, DIC dimethyltriczenormidazoleconboxamide), Hexamethylmelanine (HMM, Altretanine, Hexylin) and Procarbazine (Matulane, Natulanan).

Antimetabolite drugs are also included within the scope of the present invention, such as Azacitidine (5-azacylidine, ladakamycin) Cladribine (2-CdA, CdA, 2-chloro-2-deoxyadenosine) Cytarabine (Cytosine Arabinoside, Cytosar, Tarabine), Fludarabine (2-fluoroadenine arabinoside-5-phosphate, fludara). Fluorouracil (5-FV, Adrucil, Efuctex) Hydroxyurea (hydroxycarbamide, Hydrea), Leucovorin (Leucovorin Calcium), Mercaptopurine (G-MP, Purinethol). Methotrexate (Amethopterin), Mitoguazone (Methyl-GAG), Pentostatin (2'-deorycoformycin) and Thioguanine (6-TG, aminopurine-6-thiol-hemihydrate).

Antitumor antibiotics commonly interfere with DNA through intercalation, whereby the drug inserts itself between DNA base pairs. Introduction of ultrasound enhances this interference. Such drugs include Actinomycin DC Cosmegen. Dactinomycin), Bleomycin (Blenoxane) Daunoxubibin (rubido mycin), Doxorubicin (Adriamycin, Hydroxydaunorubicin, hydroxydaunomycin, Rubex), Idarubicin (44-demethylorydan norubicin, Idamycin), Mithramycin (Mithracin, Plicamycin). Milomycin C and Mitorantione (Novantrone).

Plant alkaloids bind to microtubular proteins thus inhibiting microtubule assembly; and ultrasound may enhance such binding. Such alkaloids include Etoposide, Paclitaxel (Taxol), Treniposide, Vinblastine (Velban, Velsar, Alkaban). Vincristine (Oncovin, Vincasar, Leurocristine) and Vindesine (Eldisine).

Hormonal agents include steroids and related agonists and antagonists, such as adrenocorticosteroids, adrenocorticosteroid inhibitors, mitolane, androzens, antiandiozens, antiestrogens, estrogens, LHRH agonists, progesterones.

Antiangiogenesiis agents include Fumagillin-derivative TNP-470, Platelet Factor 4, Interleukin-12, Metalloproteinase inhibitor Batimastat. Carboryaminatriarzole, Thalidomide, Interferon Alfa-2a, Linomide and Sulfated Polysaccharide Tecogalan (DS-4152).

The drugs that may be useful in preventing in-stent restenosis fall into four major categories; anti-neoplastics, immunosupressives, migration inhibitors, and enhanced healing factors.

Anti-proliferative compounds include Paclitaxel, QP-2, actinomycin, statins and many others. Paclitaxel was originally used to inhibit tumor growth by assembling microtubules that prevent cells from dividing. It has also recently been observed to attenuate neointimal growth.

Immunosupressives are generally used to prevent the immune rejection of allogenic organ transplants. The general mechanism of action of most of these drugs is to stop cell cycle progression by inhibiting DNA synthesis. Everolimus, Sirolimus, Tacrolimus (FK-506). ABT-578, interferon, dexamethasone, and cyclosporine all fall into this category. The Sirolimus derived compounds appear especially promising in their ability to reduce intimal thickening.

Migration inhibitors are aimed at preventing endothelial cell migration to the inside of the stent. Once smooth muscle cells migrate to the luminal side of the stent, they can produce extracellular matrix and begin to occlude blood flow. Therefore, inhibiting their migration can have great therapeutic applications for preventing in-stent restenosis. Examples of these compounds are batimastat and halofuginone. Batimastat, for example, is a potent inhibitor of matrix metalloproteinase enzymes. It can prevent the matrix degradation that is necessary for cells to free themselves to move. If the cells cannot move, they cannot invade the stent area.

Enhanced Healing Factors; Vascular endothelial growth factor (VEGF) promotes healing of the vasculature. In the context of stents, this would heal the implantation site and reduce platelet sequestration due to injury related chemotaxis. Nitrous oxide donor compounds may also replicate this effect. Healing of the vessel wall seems to be the gentlest approach to preventing ISR, but healing factors are still in the early stages of development for this application.

Sirolimus (rampamycin) and Paclitaxel are the two drugs that are commonly used in drug eluting stents. Sirolimus is a macrocyclic lactone immunosuppressive agent that inhibits the cell division cycle and cellular proliferation by promoting kinase activation and halting the cellular growth phase. Paclitaxel also inhibits the cell cycle, but works via a different mechanism than Sirolimus. Paclitaxel binds to microtubules in dividing cells and causes them to assemble, thereby preventing mitosis. Paclitaxel is in the anti-neoplastic family of compounds. Together, Paclitaxel and Sirolimus are two of the most promising drugs for use in stents, as several others have run into problems with lumen loss, late thrombosis, delayed restenosis, and aneurysm formation.

For the removal of blood clots and thrombus, examples of therapeutic agents may include (i) tissue plasminogen activator, tPA, BB-10153, rTPA, Urokinease, Streptokinase, Alteplase and Desmoteplase, (ii) antiplatelet agents such as aspirin. Clopidorgel and Ticclopidine, and (iii) GIIb/IIIa inhibitors, such as Abciximab, Tirofiban and Eptifibatide.

The devices of the present invention may be configured to release or make available the therapeutic agent at one or more treatment phases, the one or more phases having similar or different performance (e.g., delivery) profiles. The therapeutic agent may be made available to the tissue at amounts which may be sustainable, intermittent, or continuous; in one or more phases and/or rates of delivery, effective to reduce any one or more of smooth muscle cell proliferation, inflammation, immune response, hypertension, or those complementing the activation of the same. Any one of the at least one therapeutic agents may perform one or more functions, including preventing or reducing proliferative/restenotic activity, reducing or inhibiting thrombus formation, reducing or inhibiting platelet activation, reducing or preventing vasospasm, or the like.

The total amount of therapeutic agent made available to the tissue depends in part on the level and amount of desired therapeutic result. The therapeutic agent may be made available at one or more phases, each phase having similar or different release rate and duration as the other phases. The release rate may be pre-defined. In an embodiment, the rate of release may provide a sustainable level of therapeutic agent to the treatment site. In another embodiment, the rate of release is substantially constant. The rate may decrease and/or increase as desired.

These therapeutic agents may be provided and or delivered to the body in any conventional therapeutic form or formulation, such as, merely by way of example; liquid, powder, particle, microbubbles, microspheres, nanospheres, liposomes and/or combinations thereof.

Some embodiments of the invention may also include delivering at least one therapeutic agent and/or optional compound within the body concurrently with or subsequent to an interventional treatment. More specifically, the therapeutic agent may be delivered to a targeted site that includes the treatment site concurrently with or subsequent to the interventional treatment. By way of example:

a. A therapeutic agent may be delivered to the treatment site
        as a stand-alone therapy in treatment of native stenosis or restenosis, without any other contemporaneous remedy or treatment such as provided by a physical or mechanical dilation.

b. A therapeutic agent may be delivered to the treatment site as the only therapy in treatment of stenosis or restenosis in grafts.

c. A therapeutic agent may be delivered to the treatment site following any suitable interventional procedure.

d. A therapeutic agent may be delivered to the treatment site before an interventional procedure, during, after an interventional procedure, or combinations thereof.

e. A therapeutic agent may be delivered to the treatment site concurrently with a blood flow, with a partial blood flow or with no blood flow using blood flow protection devices.

The therapeutic agent may be made available to the treatment site at amounts which may be sustainable, intermittent, or continuous; at one or more phases; and/or rates of delivery.

In one aspect of the invention, improved ultrasound delivery catheters are provided that incorporate means for infusing liquid medicaments (e.g. drugs or therapeutic agents) concurrently or in conjunction with the delivery of ultrasonic energy. The delivery of the ultrasonic energy through the catheter concurrently with the infusion of therapeutic agents aids in rapidly dispersing, disseminating, distributing, or atomizing the medicament. Infusion of at least some types of liquid medicaments concurrently with the delivery of ultrasonic energy may result in improved or enhanced activity of the medicament due to: a) improved absorption or passage of the medicament into the target tissue or matter and/or b) enhanced effectiveness of the medicament upon the target tissue due to the concomitant action of the ultrasonic energy on the target tissue or matter.

Delivery of a therapeutic agent may face a different release rate during initial catheter activation compared to a normal and desirable release. Usually, the initial release of the therapeutic agent is at a higher rate/level than preferred due necessity to flesh the catheter before activation. To avoid the therapeutic agent downstream losses, distal or proximal protection or both may be used. Distal and/or proximal protection devices are known in the art, as, for example, a simple, low-pressure balloon catheter: when the balloon is expanded, it stops blood flow. In such cases when distal and/or proximal protection devices are used to prevent downstream flow of the therapeutic agent, a residual portion of the therapeutic agent may be removed or retrieved outside the body using conventional vacuum methods after exposure to the vessel wall for about one second to one hour.

Another object of the present invention is to provide an ultrasound apparatus to deliver ultrasound energy to the target tissue that utilizes at least three principal modes: longitudinal waves, shear (transverse) waves and surface (radial or elliptic) waves, among others including Lamb waves, Love waves, Stoneley waves or Sezawa waves. In longitudinal waves, the oscillation occurs in the longitudinal direction or the direction of wave propagation. In shear waves, oscillation occurs transverse to the direction of propagation. Transverse waves are relatively weak compare to longitudinal waves and are known to not effectively propagate through liquids. Surface waves are mechanical waves that propagate along the interface between differing media. Surface waves travel the surface of a solid material or liquid penetrating to a depth of one wavelength. Surface waves combine both a longitudinal and transverse motion to create an elliptic orbit motion. The major axis of the ellipse is perpendicular to the direction of the propagation of the wave.

Methods and devices of the invention that have been described above in general terms will now be described in further detail in the context of FIGS. 1-16. Referring to FIGS. 1 and 2, one embodiment of an ultrasound system 90 for delivering ultrasound and therapeutic agents for treating and/or inhibiting stenosis and/or restenosis is shown. The ultrasound system 90 includes an ultrasonic catheter device 100, which has an elongate catheter body 101, having an inside lumen/space 111. The catheter 100 comprises a proximal end 102 and a distal end 103, and an ultrasound transmission member/wire 110 disposed in the lumen 111 (FIGS. 2B and 2C).

The ultrasound transmission member or wire 110 is attached to the tip 104 on the distal end of the catheter 100 and to a connector assembly/knob 105 at the proximal end of the catheter 100. The ultrasound catheter 100 is operatively coupled, by way of a sonic connector 112 (FIG. 2A) located within the proximal connector assembly/knob 105, to an ultrasound transducer 120. The ultrasound transducer 120 is connected to a signal generator 140. The ultrasound transducer 120 may be provided inside the generator 140 (not shown). The signal generator 140 may be provided with a foot actuated on-off switch 141.

When the on-off switch 141 is turned on, the signal generator 140 sends an electrical signal via line 142 to the ultrasound transducer 120, which converts the electrical signal to vibrational energy. Such vibrational energy subsequently passes through the sonic connector 120 (inside the connector assembly/knob 105) to the catheter device 100, and is delivered via the ultrasound transmission member 110 (FIGS. 2B and 2C) to the distal tip 104. A guidewire 150 may be used in conjunction with the catheter device 100 having the entry at the distal tip 104 and exit port 151.

The generator 140 includes a device operable to generate various electrical signal wave forms such as continuous, pulse or combinations of both within frequencies range between 1 kHz and 10 MHz, and produces power of up to 20 watts at the distal end of the catheter tip 104. Thus, ultrasound energy may be provided in continuous mode, pulse mode, or any combination thereof. Also, to minimize stress on the ultrasound transmission member 110 during activation, the operational frequency of the current and/or the voltage produced by the ultrasound generator 140 may be modulated. Movement of the distal end of the drug delivery catheter may be provided in several forms vibrational energy such as longitudinal fashion, transverse fashion, radial (surface waves) fashion or a combination of all three forms. Propagation of vibrational energy from the vibrational energy source through the ultrasound catheter may be provided in the similar way. An injection pump 160 or IV bag (not shown) maybe connected by way of an infusion tube 161 to an infusion port or sidearm 109 of the Y-connector 108. The injection pump 160 is used to infuse coolant fluid (e.g. 0.9% NaCl solution) from the irrigation fluid container 162 into the inner lumen 111 of the catheter 100. Such flow of coolant fluid serves to prevent overheating of the catheter 100 during vibrational energy delivery. Due to the desirability of infusing coolant fluid into the catheter body 101, at least one fluid outflow channel 107 is located either in the distal tip 104 or in the catheter body 101 at the distal end 103 to permit the coolant fluid to flow out of the distal end of the catheter 100. Such flow of the coolant fluid through the catheter body 100 serves to bathe the outer surface of the ultrasound transmission member. The temperature and/or flow rate of coolant fluid may be adjusted to provide adequate cooling and/or other temperature control of the ultrasound transmission member. Such an irrigation procedure may also be performed by conventional syringes and other devices suitable for liquid injection.

Figure 6:
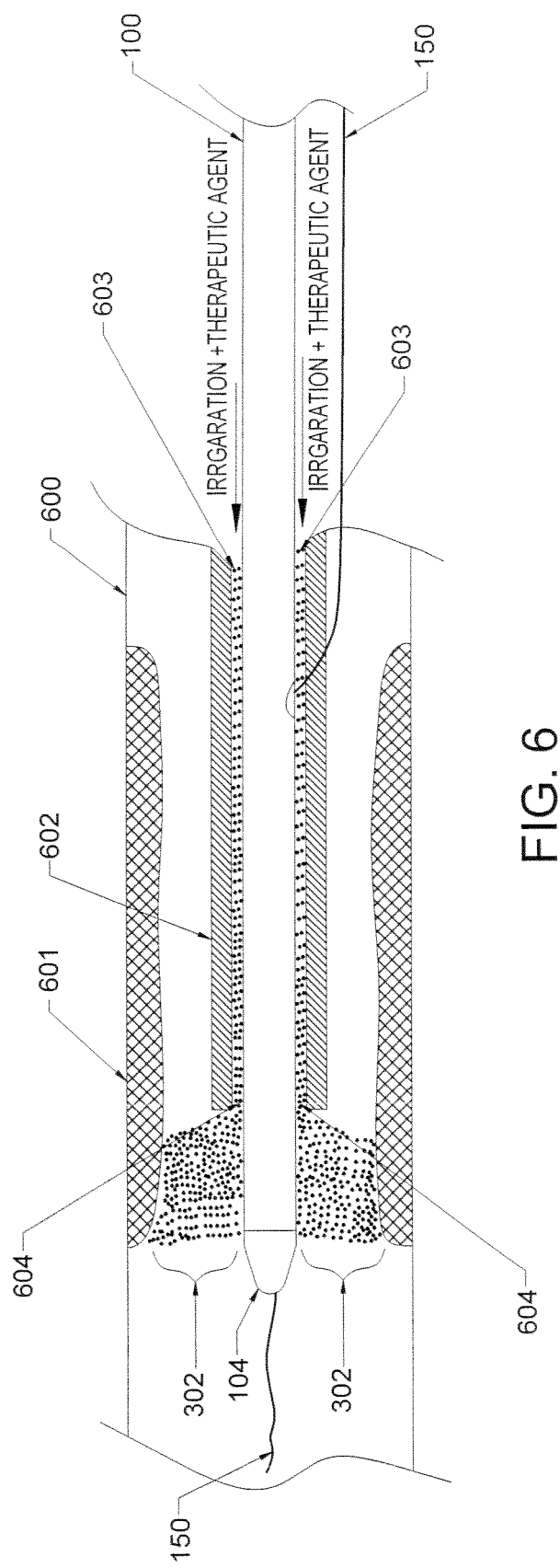
FIG. 6 shows an embodiment of an ultrasound-enhanced drug delivery catheter with and an additional sheath for delivering a therapeutic agent to a vessel to inhibit restenosis.

In addition to the foregoing, the injection pump 160 may be activated by the foot actuated on-off switch 141 at the same time as the generator 140. Therapeutic agents may be delivered together with an irrigation fluid into the catheter device 100 using the injection pump 160 and carried to the distal end 103 of the catheter 100. Therapeutic agents may be mixed, dissolved, synthesized or emulsified with other drugs solvents, liquids, or irrigation fluid and delivered to human body using injection pump 160. The injection pump 160 may also be implemented inside the generator 140 (not shown). When injected into the irrigation lumen, such therapeutic agents combined with irrigation liquid flow through the catheter inner lumen 111 and cool the ultrasound transmission member 110 of the ultrasound catheter 100 while activated. When a therapeutic agent leaves the ultrasound catheter 100 at distal end 103, it will contact and at least partially be absorbed by the blood vessel wall, Optionally, therapeutic agent may be infused separately into the catheter 100 through the other port 180 of the Y-connector 108, thus, delivering a therapeutic agent independently through a separate lumen (not shown) or not as a mixture with irrigation fluid. A therapeutic agent can be delivered into the catheter 100 through the port 180 using syringe 181 or other injection device concurrently with irrigation fluid. Optionally, a therapeutic agent may be delivered to the distal end 103 of the catheter 100 independently of the catheter 100. For example, in one embodiment, a separate lumen for a therapeutic agent inside the catheter body 101 may be provided (not shown). Alternatively, an additional sheath 602 around the catheter 100 as shown in FIG. 6 may be employed. In another alternative embodiment, a direct injection of a therapeutic drug from a guiding catheter or introducer sheath into the treatment area may be utilized.

Although the ultrasound catheter 100 in FIG. 1 is illustrated as a "monorail" catheter device, in alternative embodiments the catheter 100 may be provided as an "over-the-wire" or guidewire-free device, as are well known in the art.

Referring now to FIGS. 2A, 2B, and 2C, more detailed views of embodiments of the ultrasound catheter 100. In this embodiment, the ultrasound catheter 100 includes an elongated flexible catheter body 101 having an elongated ultrasound transmission member 110 that extends longitudinally through the inner lumen of the catheter body 111. A sonic connector 112 is positioned on the proximal end of the catheter 100 and attached to the ultrasound transmission member 110. The sonic connector 112 provides the attachment of the ultrasound catheter, more specifically the ultrasound transmission wire to an external ultrasound energy source. The sonic connector 112 is housed inside the knob 105 and is attached to the ultrasound transducer 120 when performing a procedure. While the knob 105 serves as a secondary interface between the ultrasound catheter 100 and the ultrasound transducer 120, the sonic connector 112 is securely attached to the transducer horn and transfers ultrasound vibrations from the transducer 120 to the ultrasound transmission member 110. The ultrasound transmission member 110 carries vibrational energy to the tip 104 located at the distal end of the catheter 100.

In an embodiment wherein the ultrasound catheter 100 is constructed to operate with a guidewire, an inner guidewire tube 113 may be extended within the inner lumen 111 of the catheter body 101 and attached to the tip 104 on the distal end. The other end of the guidewire tube 113 may be attached along the length of the catheter body 101. The guidewire exit port 151 may be positioned closer to the end of the catheter body or closer to the proximal end of the catheter body 100. The catheter 100 shown may be deployed with the use of the guidewire as either a "monorail" or an over-the-wire arrangement.

The catheter body 101 maybe formed of any suitable material, including flexible polymeric material such as nylon (Pebax™) as manufactured by Atochimie (Cour be Voie. Hauts Ve-Sine. France). The flexible catheter body 101 is generally in the form of an elongate tube having one or more lumens extending longitudinally therethrough.

The distal tip 104 is a substantially rigid member firmly affixed to the transmission member 110 and optionally affixed to the catheter body 101. The distal tip 104 has a generally rounded configuration and may be formed of any suitable rigid metal or plastic material, preferably radio-dense material so as to be easily discernible by radiographic means.

The tip 104 is attached to the ultrasound transmission member 110 by welding, adhesive, soldering, crimping, or by any other appropriate means. A firm affixation of the ultrasound transmission member 110 to the distal tip 104 and sonic connector 112 is required for vibrational energy transmission from the transducer 120 to the tip 104. As a result, the distal tip 104, and the distal end 103 of the catheter body 101 is caused to undergo vibrations.

The ultrasound transmission member 110 may be formed of any material capable of effectively transmitting the ultrasonic energy, such as, by way of example, metal, fiber optics, polymers, and/or composites thereof. In some embodiments, a portion or the entirety of the ultrasound transmission member 110 may be formed of one or more shape memory or super elastic alloys. Examples of super-elastic metal alloys that are appropriate to form the ultrasound transmission member 30 of the present invention are described in detail in U.S. Pat. No. 4,665,906 (Jervis). U.S. Pat. No. 4,565,589 (Harrison), U.S. Pat. No. 4,505,767 (Quin), and U.S. Pat. No. 4,337,090 (Harrison). The disclosures of U.S. Pat. Nos. 4,665,906; 4,565,589; 4,505,767; and 4,337,090 are expressly incorporated herein by reference as they describe the compositions, properties, chemistries, and behavior of specific metal alloys which are super-elastic within the temperature range at which the ultrasound transmission member 110 of the present invention operates, any and all of which super-elastic metal alloys may be usable to form the super-elastic ultrasound transmission member 110.

A therapeutic agent is infused through the inlet port 109 of the Y-connector 105 and the lumen 111 of the catheter body 101 when delivered as mixture with an irrigation fluid (FIG. 1). If a therapeutic agent is infused separately, the port 180 may be used. The outlets ports for the therapeutic agent from the catheter 100 either when drug is delivered as a mixture with the irrigation fluid or separately through the port 180 are located at the distal end 103 of the catheter 100. In some embodiments, outlet ports 106 are located in the distal tip 104 only, and are positioned to deliver a therapeutic agent (and irrigation fluid) in a radial manner, around the distal tip. In another embodiment, outlet ports 107 maybe located in the wall of the catheter body 101 at its distal portion 103.

Various other arrangements and positioning of the respective drug/irrigation outlet ports 106 and 107 may be utilized in other embodiments of the invention. The size and number of these outlet ports may vary depending on the specific intended function of the catheter 100, the volume or viscosity of the therapeutic drug intended to be infused, and/or the relative size of the therapeutic area to which the drug is to be applied. In other embodiments, outlet ports may be located in both mentioned locations as shown in FIG. 2C. In some embodiments, outlet ports are located in such order that irrigation liquid and therapeutic drug are distributed evenly around the distal end 103, and in such fashion that the same volume and pressure at each outlet port are achieved to assure uniform distribution and application of a therapeutic drug to the vessel wall.

Figure 3C:
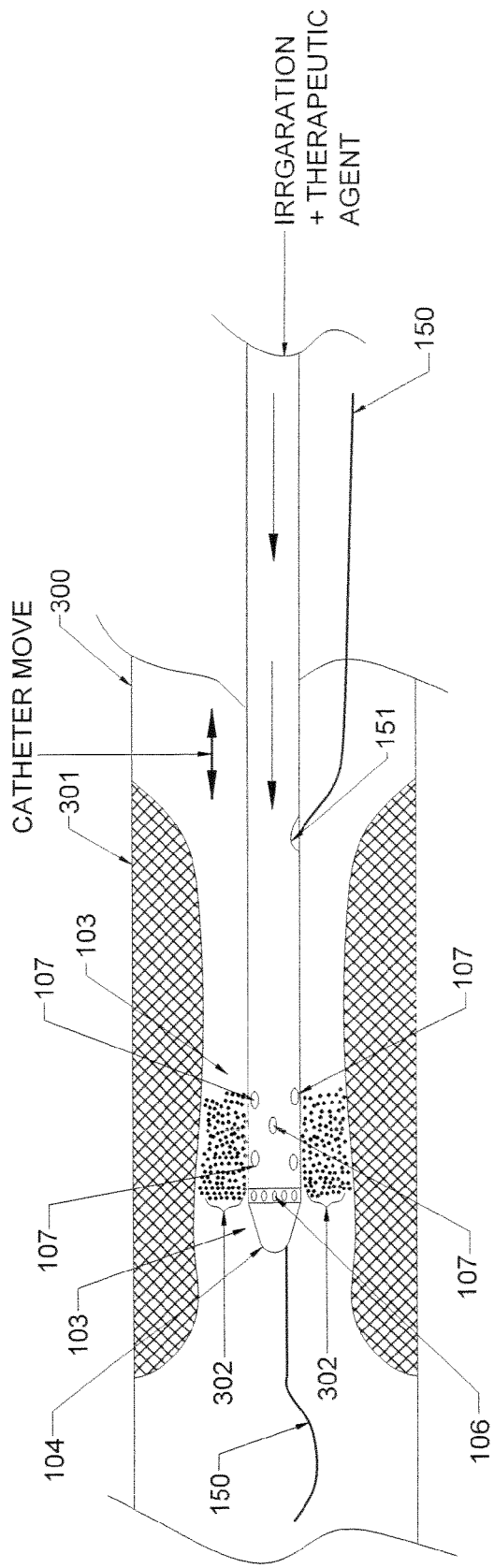

With reference now to FIGS. 33A, 3B, and 3C, in some embodiments of the invention, a therapeutic agent may be delivered to a vascular stenosis site as a stand-alone treatment (i.e., without contemporaneous angioplasty, venoplasty or stenting). Such a separate therapeutic agent therapy may be used, for example, when the vascular stenosis has not closed a vessel by more than 50% and there is no significant blood flow disturbance effect in supplying blood to surrounding areas and organs. Alternatively, to improve the final result, in some embodiments a conventional angioplasty or venoplasty procedure such as balloon angioplasty or venoplasty, stent, atherectomy, laser treatment or combinations of these therapies may be used before or after a therapeutic agent delivery procedure.

In FIG. 3A, the distal end 103 of the ultrasound catheter 100 is introduced inside the vessel 300 over the guidewire 150 and positioned within the stenosis or treatment area 301. The distal tip 104 of the ultrasound catheter 100 has a series of radial holes 106 that serve as outlet ports for irrigation fluid and therapeutic drug. When ultrasound energy is delivered to the catheter 100, the distal tip 104 vibrates causing the irrigation fluid and therapeutic drug passing out of the catheter 100 to mix together, to be pulverized into droplets 302, and to disperse outward, all of these effects increasing permeation of the drug into the vessel wall. Also, the vibrating tip 104 of the ultrasound catheter 100 may cause local vasodilatation or sonophoresis around the surrounding tissue, thereby creating micro indentation in the treatment area 301 due to cavitation, increasing its permeability, and allowing the applied drug to penetrate better into the vessel wall. Delivery of ultrasound energy from the tip 104 to the treatment area 302 promotes intracellular activation of cells by irradiating tissue with ultrasound energy to cause an improved passage of a therapeutic drug into the treatment area 301.

To cover a larger area of treatment, the catheter tip 104 may be repositioned within the vessel 300, either longitudinally, radially, or by both orientations as required. The catheter 100 may also be rotated within the vessel 300 if desired. The embodiment of FIG. 3B differs from that of FIG. 3A in that therapeutic agent outlet ports 107 are located in the wall of the catheter body 101 instead of at the tip 104 as shown in FIG. 3A. The embodiment in FIG. 3C shows the provision of both types of outlet ports 106, 107 as illustrated in FIG. 3A and FIG. 3B combined. During ultrasound energy delivery, outflow mixture of the irrigation fluid and therapeutic drug from ports 106 and 107 is being dispersed, pulverized into droplets 302 and delivered to the treatment site 301.

Alternative embodiments of devices and methods of the invention (not shown) include applying or coating the therapeutic agent to the exterior of a balloon that is attached to the distal end of the ultrasound catheter. Inflation of the balloon enables approximation of the therapeutic drug to the vessel wall and at least partial stasis of the blood flow through the blood vessel. In combination with balloon inflation, ultrasound energy at the catheter tip is activated which may cause local vasodilatation or sonophoresis around the surrounding tissue to enable greater penetration of the drug delivery. Also, ultrasound energy in combination with the fluid elements on the inside lining of the blood vessel may enable transformation of the drug coating from the balloon to the blood vessel.

Other alternative embodiments of devices and methods for the present invention (not shown) include the use of a porous balloon attached to the end of the ultrasound catheter. In these embodiments, the balloon is inflated with the therapeutic agent inside, and the balloon weeps the therapeutic drug as the pressure inside the balloon increases. While the drug weeps through the balloon materials or through small holes in the balloon, ultrasound energy is activated to enable local vasodilatation or sonophoresis around the surrounding tissue to aid in increased drug penetration into the targeted blood vessel.

Still other alternatives embodiments of devices and methods the invention (not shown) include ultrasound-assisted delivery of therapeutic agents that are delivered either, before, during or after the endovascular recanalization step, to improve arterial stenosis or restenosis, Types of stenosis that could be treated by this technology and method include minor atherosclerotic disease to chronic total occlusions (CTO). Recanalization of the vessel can be achieved by a multitude of ablation technologies (e.g. ultrasound, atherectomy, radiofrequency) or mechanical means (e.g., balloon). In one specific example, the same ultrasound device may be used both to ablate the CTO and to assist delivery of the therapeutic agent to the vessel wall while recanalizing the CTO site. Also, as another alternative, after the initial recanalization and delivery of therapeutic agent to the target tissue, a follow up therapy such as balloon angioplasty, venoplasty, stent or other may be employed.

Yet further alternative embodiments of devices and methods the invention (not shown) include the use of a mesh device that is made of metal, polymer, or a combination of such materials that is attached to the end of the ultrasound catheter. Such mesh devices may be used in a similar way as the balloon devices described above, either coated or not coated with a therapeutic agent.

In most cases, ultrasound enhanced drug delivery to treat stenosis and restenosis may be applied to existing atherosclerotic disease. However, it may also be used in some embodiments as a preventive measure in areas that are vulnerable to atherosclerotic disease or stenosis generally, such as an area referred to as a "vulnerable plaque".

Figure 4A:
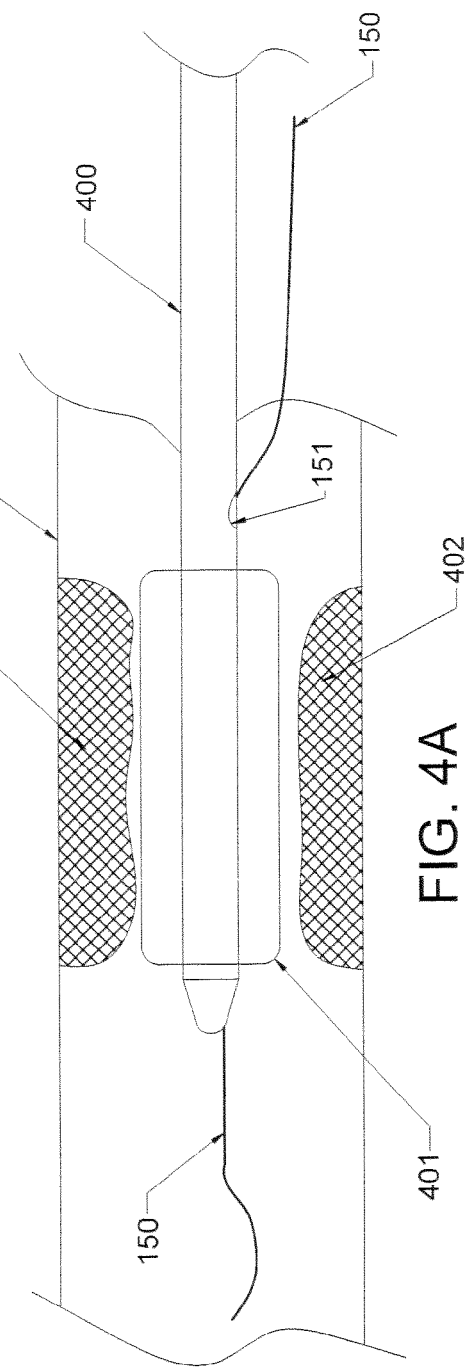
FIG. 4A shows an embodiment of an ultrasound-enhanced drug delivery catheter positioned for a balloon angioplasty or venoplasty procedure prior to ultrasound-enhanced drug delivery to a stenotic site.

Referring now to FIGS. 4A and 4B, one embodiment of the method of the invention may include first performing a conventional angioplasty or venoplasty (FIG. 4A) and then delivering a therapeutic agent (FIG. 4B). In this embodiment, as shown in FIG. 4A, a balloon catheter 400 having a balloon 401 is introduced over the wire 150 inside the vessel 400 to the treatment area 402. FIG. 4B shows a previously diseased area 402 compressed by the balloon 401 inflation. The ultrasound catheter 100 is introduced over the same guidewire 150 to a newly reconfigured disease area 410 (post balloon angioplasty or venoplasty). A therapeutic agent is delivered to the distal end of the ultrasound catheter 100 having outlet ports 106 located in the tip 104, and outlet port 107 located in the wall of the catheter body 101. The mode of operation and action is the same as that described in FIGS. 3A, 3B, and 3C.

In other embodiments of the invention, as shown in FIG. 5, a stenosis treatment system 500 may include an ultrasound/drug delivery catheter 520 coupled with a distal flow protection device 501 to prevent downstream flow of blood and therapeutic drug. In this embodiment, a low-pressure compliant balloon 502 is mounted on the distal end of the protection device 501, in this case a small, guidewire size device. One current example of such device is the PercuSurge Guardwire® (Medtronic/PercuSurge, Minneapolis, Minn.). The balloon 502 is inflated accordingly and the ultrasound energy enhanced drug delivery is performed as described in FIGS. 3A-3C. The balloon 502 of the protection device 501 may be fully inflated as shown in FIG. 5, so that no therapeutic drug is delivered beyond the treatment site 510. If desired, the balloon 502 may be deflated and inflated to allow ultrasound enhanced drug delivery to a whole length of the treatment area 510. Such blood flow protection feature may be achieved also by installing a similar balloon onboard the ultrasound catheter 100, proximal to therapeutic agent outlets. An example of such a device is described by Passafaro et al. (U.S. Pat. No. 5,324,255). A balloon feature described by Passafaro et al., onboard the ultrasound device may serve two functions, as an angioplasty or venoplasty device and as a blood flow protection device, as desired. Also, blood flow protection at the treatment area may be achieved using a proximal protection device such as guiding catheter with a balloon onboard. These devices are known in the art and will not be described further.

An alternative embodiment (not shown) to prevent downstream flow of blood and therapeutic drug is inflating a balloon or a mesh device proximal to the ultrasound drug delivery location. Such a balloon or mesh device can be integrated with the ultrasound/drug delivery or be a separate catheter device. Use of a balloon or mesh elements in any of the embodiments described in this application can be used to prevent downstream delivery of the drug and to enable faster delivery, or the delivery of greater amounts, of drug to the targeted tissue.

An alternative embodiment (not shown) to prevent downstream flow of blood and therapeutic drug migration when a flow protection device is used may include retrieving residual mixture of drug/blood/solvent outside the body to minimize any systemic toxic effect.

FIG. 6 shows another embodiment of the present invention. The ultrasound catheter 100 is delivered to the diseased area 601 inside the vessel 600 over the wire 150. An additional single lumen sheath 602 is positioned over the ultrasound catheter 100. A therapeutic agent is delivered from an independent source and separately from the irrigation system of the catheter 100. The additional sheath 602 is a single lumen catheter having an inner lumen 603 extending longitudinally, and is positioned over the ultrasound catheter 100, A therapeutic agent is delivered through the lumen 603 and exits the sheath 602 at the distal end 604 thereof which is positioned in the vicinity of the distal end 103 of the ultrasound catheter 100. Activation of the ultrasound catheter 100 causes the catheter distal tip and the immediate area of the catheter 100 distal portion 103 to vibrate. Vibrations of the distal end 103 causes a therapeutic drug delivered from the distal end of the sheath 602 to be pulverized into droplets 302 and delivered to the treatment site 601. Also, a vibrating tip 104 of the ultrasound catheter 100 may continue to induce local vasodilatation around the surrounding tissue 602, further increasing its permeability, so that the applied drug penetrates into the vessel wall. Due to the nature of therapeutic drug supply from the sheath 602, a flow protection may be appropriate.

Any of the therapeutic agents detailed above may be introduced to a treatment site using the methods and devices described herein, with or without coolant fluid (e.g., 0.9% NaCl solution). Alternatively or additionally, in other embodiments, a therapeutic agent may be delivered along with a contrast agent, such as an angiographic contrast agent, for diagnostic purposes. Any suitable contrast agent may be used in combination with a therapeutic agent of the present invention, delivered together or separately, either with contrast agent diluted with the 0.9% NaCl solution or at 100% concentration. Also, a therapeutic agent may be delivered in solution with Carbamide [$(NH_2)_2CO$] into the artery or vein to the treatment location.

An illustrative clinical example of an application of the invention will now be provided, in which the described ultrasound enhanced delivery of therapeutic agent is applied to the treatment of a patient with a stenotic coronary artery or vein. Following the diagnosis of a chest pain or angina in the patient, it is radiographically determined that the left coronary artery or vein is significantly occluded and that blood flow to the left side of hart is impaired. A coronary guide catheter is inserted percutaneously into the patient's femoral artery or vein and such guide catheter is advanced and engaged in the left coronary ostium. A guide wire is advanced through the lumen of the guide catheter to a location where the distal end of the guidewire is advance directly through or immediately adjacent to the obstruction within the left coronary artery. An ultrasound catheter 100, an embodiment of the present invention, as shown in FIGS. 1-6, is advanced over the pre-positioned guide wire 150 by inserting the exteriorized proximal end of the guide wire into the guide wire passage formed in the distal tip 104 of the catheter 100. The catheter 100 is advanced over the guide wire 150, such that the proximal end of the guide wire 150 emerges out of guide wire exit port 151. The ultrasound catheter 100 is advanced to the coronary obstruction to be treated as shown in FIGS. 3A-3C. Thereafter, a container 162 of sterile 0.9% NaCl solution may be connected, by way of a standard solution administration tube 161 to the coolant infusion side arm 109 and a slow flow of saline solution is pumped or otherwise infused through sidearm 109, through the lumen 111 of the catheter body 101 and out of outlet ports located at the tip 104 or the distal portion 107 of the catheter body 101, as shown in FIG. 3B. An intravenous infusion pump 160 is then used to provide such flow of coolant fluid through the catheter. The proximal connector assembly 105 of the catheter 100 is then connected to the ultrasound transducer 120 via sonic connector 112, and the ultrasound transducer 120 is correspondingly connected to the signal generator 140 so that, when desired, ultrasonic energy may be passed through the catheter 100. A therapeutic agent is mixed with a sterile 0.9% NaCl coolant solution and delivered from the bottle 162 and tube 161 to the coolant infusion port 109 of the catheter 100. Alternatively, a therapeutic agent may be injected through the other port 180 and syringe 181, separately from the coolant fluid.

To initiate delivery of a therapeutic agent, the flow of coolant infusion mixed with a therapeutic agent is delivered from the bottle 162 to the infusion port 109 and maintained at an appropriate flow rate while the signal generator 140 is activated by compression of on/off foot pedal 141. When actuated, electrical signals from the signal generator 140 pass through cable 142 to ultrasound transducer 120. Ultrasound transducer 120 converts the electrical signals into ultrasonic vibrational energy and the ultrasonic energy is passed through the ultrasound transmission member of the catheter 100 to the distal tip 104 and its distal portion 103. The distal portion 103 of the catheter 100 may be moved, repositioned back and forth by the operator to deliver therapeutic agent to the entire treatment site thereby treating the stenosis of the occluded left coronary artery. After the ultrasonic enhanced delivery of a therapeutic agent has been completed, and after the desired dose of drug has been delivered through the catheter 100 to the treatment site 301, the infusion of irrigation fluid and therapeutic agent is ceased and the signal generator 140 de-actuated. Thereafter, the ultrasound catheter 100 and guidewire 150 are extracted from the coronary artery, into the guide catheter and outside the body, and then, the guide catheter is retracted and removed from the body. The ultrasound enhanced delivery of a therapeutic agent is considered as the first line therapy Referring now to FIGS. 7A and 7B, another method according to the present invention may include first performing a conventional angioplasty or venoplasty, which is represented by a reconfigured diseased area 701 (post balloon angioplasty or venoplasty), then delivering only a therapeutic ultrasound energy using the ultrasound catheter 100 as shown in FIG. 7A. The ultrasound catheter 100 is capable of delivering therapeutic agent, but in this embodiment emits only ultrasound energy to the vessel wall around diseased area 701 in the form of sonic waves 702. Ultrasound energy application may be provided by any other suitable ultrasound catheter. The ultrasound catheter 100 can be repositioned within the vessel back and forth over the guidewire 150 as shown by the double arrow 703 to cover a whole area of treatment and to create desirable sonoporation and vasodilatation effects for a better drug permeability into the vessel wall. After delivery of ultrasound energy, the ultrasound catheter is removed and a conventional drug delivery catheter 710 as shown in FIG. 7B is introduced over the guidewire 150 to a newly treated area after the initial ultrasound exposure to the area 701. A therapeutic agent is delivered from an independent source, such as through drug outlets 715 at the distal end of a drug delivery catheter 710. The drug delivery outlets 715 are positioned in the vicinity of the newly modified treatment area 720, and the therapeutic agent 716 is delivered to the vessel wall. The drug delivery catheter maybe reposition back and forth in the vessel as shown by the double arrow 704 represent the entire treatment area 720, and until the application of the therapeutic agent is completed. Due to the nature of certain therapeutic drugs, a flow protection may be appropriate (not shown) for such drugs.

Figure 8A:
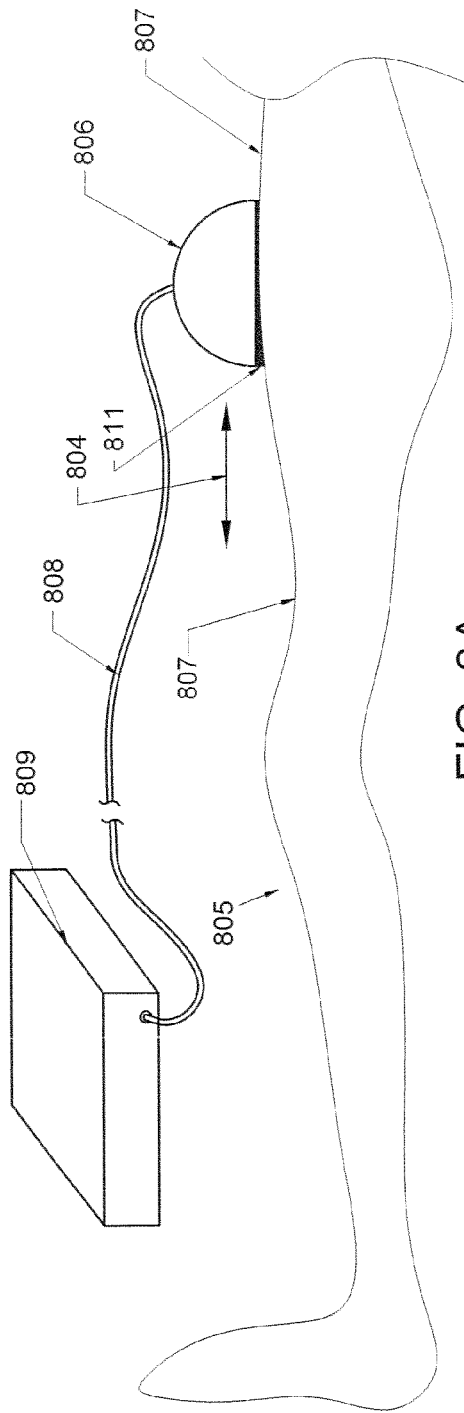
FIG. 8A shows a general view of an ultrasound-enhanced drug delivery using an external ultrasound source and a transcutaneous method to deliver ultrasound energy to the treatment area.
Figure 8B:
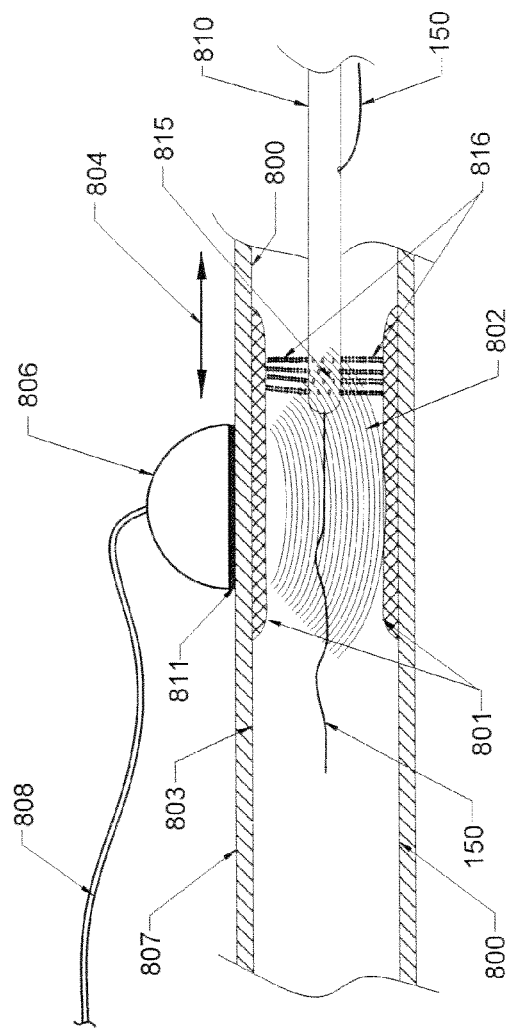
FIG. 8B shows an embodiment of an ultrasound-enhanced drug delivery using external ultrasound source and a transcutaneous method to deliver ultrasound energy to the treatment area, and further showing endovascular catheter to deliver a therapeutic agent.

Also, all above described embodiments related to the application of a therapeutic agent to the vessel wall may be carried out in conjunction with emitting ultrasound energy to the vessel wall from an external ultrasound device in a transcutaneous fashion as shown in FIGS. 8A and 8B. FIG. 8A shows a human lower extremity (e.g., leg) 805 with an external ultrasound transducer 806 positioned on the skin 807 around the treatment area. The external ultrasound energy source can be a transducer 806 connected via a cable 808 to an ultrasound generator 809. The ultrasound generator 809 converts line power into a high frequency current that is delivered to the transducer 806. The transducer 806 comprises piezoelectric crystals that convert high frequency current into ultrasonic energy that is delivered into the leg 805 through the skin 807. The generator 809 includes a device operable to generate various electrical signal wave forms such as continuous, pulse or combinations of both, within a frequency range between 1 kHz and 10 MHz, and can produce a power output of up to 100 watts at transducer 806. The ultrasound energy may be provided in continuous mode, pulse mode, or any combination thereof. Also, to improve efficacy and minimize stress as well as reduce a potential thermal damage to the skin 807 between the transducer 806 and the surrounding skin area during ultrasound energy activation, the operational frequency, as well as current/voltage produced by the ultrasound generator 809, as well as timing/pulsing may be modulated. In addition, ultrasound transmission gel 811 (e.g. such as that manufactured by Graham-Field, Bay Shore, N.Y.) may be used between the transducer 806 and the skin 807 to reduce skin burns. A non-limiting example of a suitable ultrasound device includes the TIMI3 Transcutaneous System (Santa Clara, Calif.). As shown in FIG. 8B, the transducer 806 produces ultrasound waves 802 that propagate through the skin 807 and leg tissue 803 to the treatment area 801 of the vessel 800. The treatment area 801 may often be a reconfigured diseased area after initial angioplasty or venoplasty. The drug delivery catheter 810 is positioned over the guidewire 150 inside the vessel 800 around the treatment area 801. A therapeutic agent 816 is delivered through the distal outlet ports 815 of the drug delivery catheter 810 in a radial fashion towards the treatment area 801. The therapeutic agent 816 can be delivered before, during and after ultrasound energy delivery from the transducer 806. The vibrating transducer 806 produces sound waves 802 that penetrate through the leg skin 807 and the tissue 803 to the treatment area 801, and induces local vasodilatation and sonoporation within the surrounding tissue, further increasing its permeability, so that the applied drug penetrates into the vessel wall. Radial waves may also impact surrounding vessels that are away from the vibrational energy source since such waves tend to penetrate and propagate up to one wavelengths distance from vibrational source. Consequently, other vessels in the area where such vibrational energy is applied may also demonstrate increased permeability. When therapeutic drugs are applied to such non-diseased areas (either intended or not intended), it may also show angiogenesis.

Figure 9:
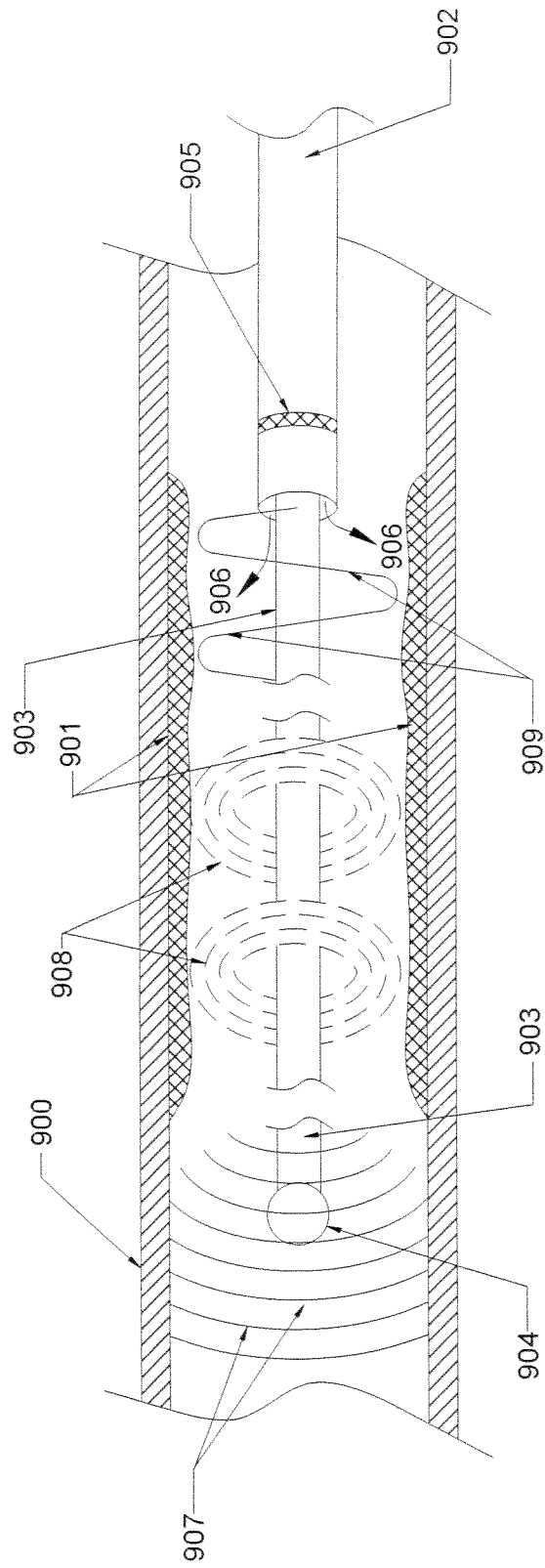
FIG. 9 shows an ultrasound device having a flexible distal member to deliver ultrasound energy to the treatment area to improve vessel drug permeability.

FIG. 9 illustrates another method to deliver ultrasound energy to the treatment area to enhance vessel permeability according to the present invention. An ultrasound catheter 902 has a distal ultrasound flexible member or probe 903 with a distal rounded, non-traumatic tip 904, Ultrasound energy produced by the generator 140 and the transducer 120 as shown in FIG. 1 is delivered through the ultrasound transmission member 110 as shown in FIGS. 2B and 2C. The transmission member 110 has a flexible distal member 903 that is located outside the ultrasound catheter 902. The ultrasound catheter 902 and distal flexible member 903 are positioned within the treatment (diseased) area 901 inside the vessel 900. The entire length of the flexible member 903 is exposed to the diseased (stenosis, plaque) area 901 inside the vessel 900. There is a distal marker 905 located on the end of the catheter 902 which provides positioning and visualization under fluoroscopy for the catheter 902 and flexible member 903.

As used herein, three modes of propagated ultrasound energy (longitudinal waves 907, transverse waves 909 and surface waves 908) may be delivered along the flexible member 903. While it is difficult to show schematically all these three sound waves simultaneously, FIG. 9 provides representative wave illustrations that serve for explanation purpose only and which do not limit the claims made herein.

The entire length of the flexible member 903 serves as an active member that delivers ultrasound energy to the adjacent diseases area 901. The injection pump 160 is used to infuse coolant fluid (e.g., 0.9% NaCl solution) from the irrigation fluid container 162 (as shown in FIG. 1) into the inner lumen 906 of the catheter 902. Such flow of coolant/irrigation fluid serves to prevent overheating of the ultrasound transmission member 110 and flexible member 903 during ultrasound energy delivery. In addition, once the irrigation fluid leaves the inner lumen 906 of the catheter 905, it works as a medium to propagate longitudinal waves 907, surface waves 908 and transverse waves 909 toward the adjacent tissue 901. Other ultrasound waves are also propagated from the ultrasound transmission member 110, but play a less important role in changing plaque compliance and increasing vessel permeability.

The flexible member 903 can be made from any metal suitable to propagate ultrasound energy, and preferably has a circular shape having a diameter anywhere between 0.1 mm to 5 mm and a length that can vary anywhere between 0.1 mm and 500 mm. The operational frequency for the flexible member can be between 1 Hz-10 MHz. Despite the fact that ultrasound energy is commonly defined as vibrations that occur at a frequency above the audible range (17-20 kHz), a more suitable term for frequency below and above this range is vibrational energy.

While the time of ultrasound energy exposure depends on vessel size and the severity of the disease, the exposure time within the treated area can be anywhere between 1 second to 60 minutes. Ultrasound power delivered to the vessel wall should not exceed 20 Watts to avoid tissue damage.

The method described in FIG. 9 may also be used to treat stenosis, restenosis of heart valves either calcific or non-calcific. In such application, a diseased area 901 may be located on the surface of the heart valve and surrounding tissue.

Figure 10:
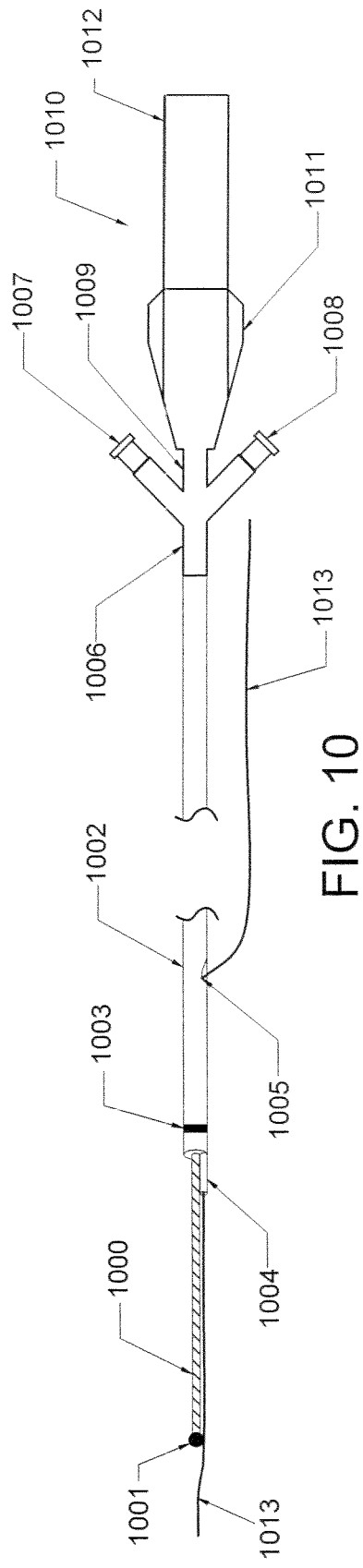
FIG. 10 shows an ultrasound device with a distal ultrasound transmission member according to another embodiment of the present invention.
Figure 11:
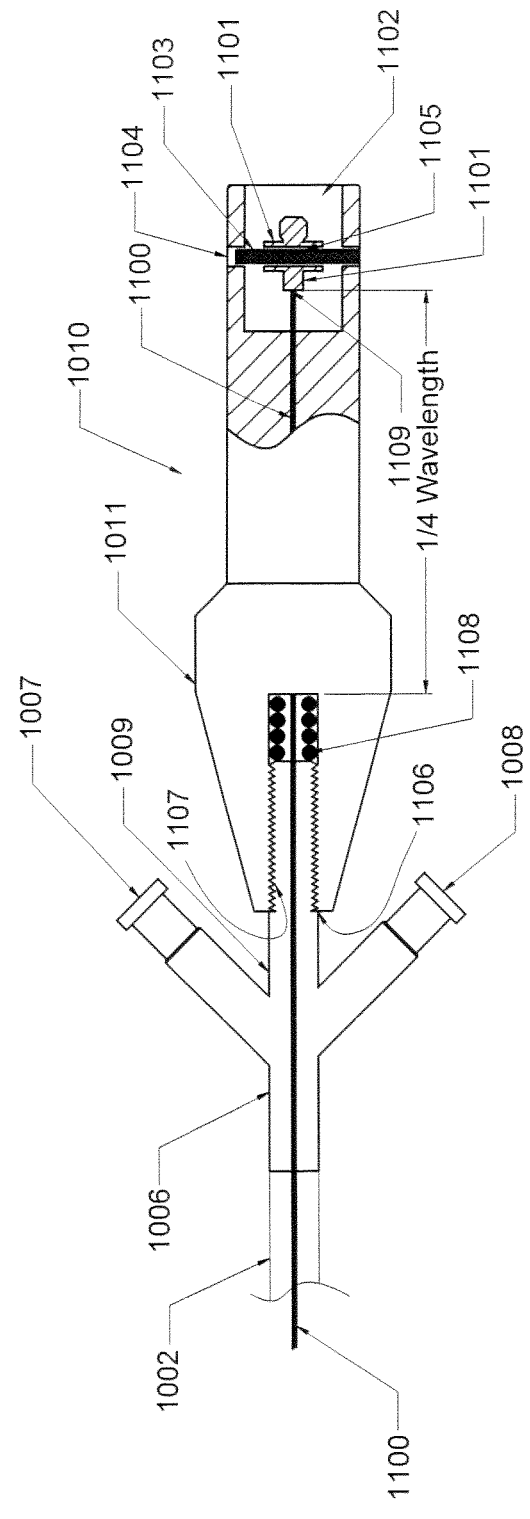
FIG. 11 is a partial cross-sectional view of the proximal portion of the ultrasound device shown in FIG. 10.

FIG. 10 illustrates another catheter device according to the present invention. The catheter device comprises an ultrasound transmission member 1000 having a distal tip 1001, a catheter body 1002 having a radiopaque marker 1003 and an attached guidewire lumen 1004 having a proximal exit port 1005. Connected to the proximal end of the catheter body 1002 are a proximal connector 1006 having three ports 1007, 1008 and 1009, and a proximal knob 1010 having a distal portion 1011 and proximal portion 1012. A guidewire 1013 is extended through the guidewire lumen 1004 and the guidewire exit port 1005. The guidewire 1013 and guidewire lumen 1004 are shown for reference only as the present invention can be applied to both catheters that include and not include a guidewire. The catheter body 1002 can be formed of any polymeric material. The flexible catheter body 1002 is preferably an elongate tube having one or more lumens extending longitudinally. The distal portion of the three arm connector 1006 is connected to the proximal end of the catheter body 1002 using techniques that are well-known in the catheter art. Extending longitudinally through the lumen of the catheter body 1002 is the elongate ultrasound transmission member 1000. The proximal end 1100 of the ultrasound transmission member is extended through the proximal end of the catheter body 1002, three arm connector 1006 and knob 1010 (as shown in FIG. 11), and the very proximal end of the ultrasound transmission member 1100 is connected to the sonic connector 1101 (see FIG. 11), which is removable connectable to the ultrasound transducer (not shown). With such an arrangement, ultrasound energy passes from the ultrasound transducer (not shown) through the sonic connector 1101, the proximal end of the ultrasound transmission member 1000, and is delivered to the distal tip 1001 of the ultrasound transmission member 1000 as shown in FIG. 10. In one embodiment, the ultrasound transmission member 1000 may be formed of any material capable of effectively transmitting the ultrasonic energy, and is preferably made from metals including but not limited to: titanium, aluminum and their alloys. Also, the ultrasound transmission member 1000 can be formed with one or more materials which exhibit super-elasticity. Examples of super-elastic metal alloys which are usable to form the ultrasound transmission member of the present invention are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison). The disclosures of U.S. Pat. Nos. 4,665,906; 4,565,589; 4,505,767; and 4,337,090 are expressly incorporated herein by reference.

FIG. 11 illustrates the details of the proximal part of the catheter device shown in FIG. 10. The distal portion 1011 of the knob 1010 has a partially threaded bore 1106. The port 1009 of the three arm connector 1006 also has external threads 1107 and is attached to the distal end 1011 of the catheter knob 1010 by threadably engaging the threaded part 1107 of the port 1009 inside the bore 1106. An injection pump, IV bag or syringe (not shown) can be connected to an infusion port or sidearm 1007 of the three arm connector 1006. The injection pump, IV bag or syringe can be used to infuse coolant fluid into and/or through the lumen(s) of the catheter body 1002. Such flow of coolant fluid may be utilized to prevent overheating of the ultrasound transmission member 1000. The port 1008 of the three arm connector 1006 may serve to deliver therapeutic agents and to aspirate drugs after use if needed. It also can be used to evacuate ablated plaque and blood clots. The very proximal end of the ultrasound transmission member 1000 is attached to a sonic connector 1101 which is configured to couple the proximal end of the ultrasound transmission member 1000 to the horn of the ultrasound transducer located inside the transducer housing 120 as shown in FIG. 1. The proximal portion 1012 of the knob 1010 has a bore 1102 that accommodates the sonic connector 1101. The sonic connector 1101 is attached to the proximal end of the ultrasound transmission wire 1000 at a joint 1109 using conventional methods such as crimping welding, soldering or bonding. The sonic connector 1101 is positioned within the bore 1102 with a pin 1103 placed through a hole 1104 in the proximal portion 1012 of the knob 1010. The sonic connector 1101 has also a through-hole 1105 which accommodates the pin 1103 and secures the sonic connector 1101 inside the bore 1102 in a position aligned with the pin 1103. The sonic connector 1101 has some freedom to move around the pin 1103, so it can freely vibrate and propagate ultrasound energy to the ultrasound transmission member 1000.

The ultrasound catheter shown in FIG. 10 is configured to propagate ultrasound energy along the proximal end 1100 and produce mostly longitudinal and surface waves along the ultrasound transmission member 1000, and to further propagate surface waves to the surrounding tissue directly or through irrigation medium. To achieve the most optimal edifice, an absorber in the form of a series of polymer o-rings 1108 or other means for mitigating transverse motions, such as elastic element(s), can be positioned inside the proximal bore 1106 of the knob 1011 and between the bottom of the bore 1106 and the distal end of the threaded part 1107 of the port 1009. A preferable location for positioning the o-rings 1108 is outside the ¼ λ (one-quarter wavelength) distance from the sonic connector 1101 as shown in the FIG. 11. Such a positioning will reduce transverse motions while allowing longitudinal motions to propagate through the ultrasound transmission member 1000. The number of o-rings 1108, or the length and size of other elastic element(s), can be selected depending on the intensity requirement of the surface waves along the ultrasound transmission member 1000.

Figure 12:
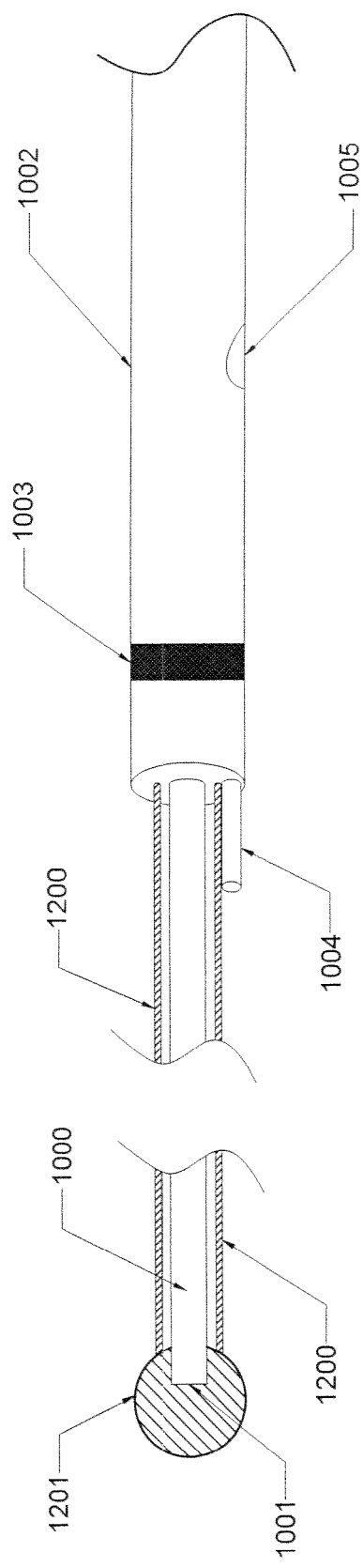

FIG. 12 shows an alternative structure of ultrasound transmission member 1000. As described above, the distal ultrasound flexible member 1000 may undergo some undesired transverse motions that may cause the ultrasound transmission member 1000 to break or experience failure. To reduce such potential problems and related clinical challenges, a polymer sheath 1200 can be positioned along the ultrasound transmission member 1000. Such a polymer sheath 1200 will allow ultrasound energy in form of longitudinal waves to propagate to the distal tip 1001 of the ultrasound transmission member 1000, while reducing transverse motions, thereby generating surface waves along the ultrasound transmission member 1000 and further propagating these surface waves to the treatment area. In addition, a polymer shell 1201 maybe added or fused around the distal tip 1001 for further tissue protection since a significant amount of heat may be concentrated around this very distal area of the ultrasound transmission member 1000 during ultrasound energy delivery. Polymer materials that can be used for both the polymer sheath 1200 and the polymer shell 1201 may include but is not limited to; PTFE, PTE, polyurethane, polyamide, polyethylene or nylon. The polymer sheath 1200 may also be further extended proximally into the catheter body 1002. The catheter body 1002 may be repositioned along the ultrasound transmission member 1000 as required by the length of the treated area. The catheter body 1002 includes a guidewire lumen 1004 that may be extended beyond the distal end of the catheter body 1002. The guidewire exit port 1005 of the guidewire lumen 1004 may be positioned at, or exit at, any desired location along the catheter body 1002, including at the three-arm connector 1106 and the knob 1010. The polymer material used for the polymer shell 1201 and the polymer sheath 1200 can be mixed with a radiopaque metallic powder to provide a better visibility of the ultrasound transmission member 1000 and the distal tip 1001 under fluoroscopy.

The ultrasound transmission member 1000 is configured to propagate ultrasound energy in form of surface waves along the length of the ultrasound transmission member 1000 that is exposed to the treatment area, and located between the distal tip 1001 and the distal end of the catheter 1002. The ultrasound transmission member 1000 can have at least two regions of a different (decreasing) cross-sectional dimension (not shown) to maintain a desired flexibility adjacent the distal end and durability at the proximal end. The ultrasound transmission member 1000 extends longitudinally through the catheter 1002 and is connected to the sonic connector 1101 as shown in FIG. 11. The ultrasound transmission member 1000 may be tapered or narrowed, or have an increased cross-sectional dimension so as to generally decrease the rigidity of the ultrasound flexible member 1000 and to cause amplification of the ultrasound energy transmitted to the distal portion of the ultrasound transmission member 1000. The ultrasound transmission member 1000 may have a plurality of intermediate tapered sections, progressively tapered sections or a combination of both, having diameters that progressively decrease from the area adjacent to the proximal region toward the distal region. The ultrasound transmission member 1000 may also include a continuous diameter or tapered structure, while the distal tip 1001 of the flexible member may be larger, smaller, or have the same dimension as the intermediate dimension of the ultrasound transmission member 1000. The proximal end 1100 of the ultrasound transmission member 1000 as shown in FIG. 11 may include any dimensional configuration required to optimize ultrasound energy delivery to the ultrasound transmission member 1000.

Figure 13:
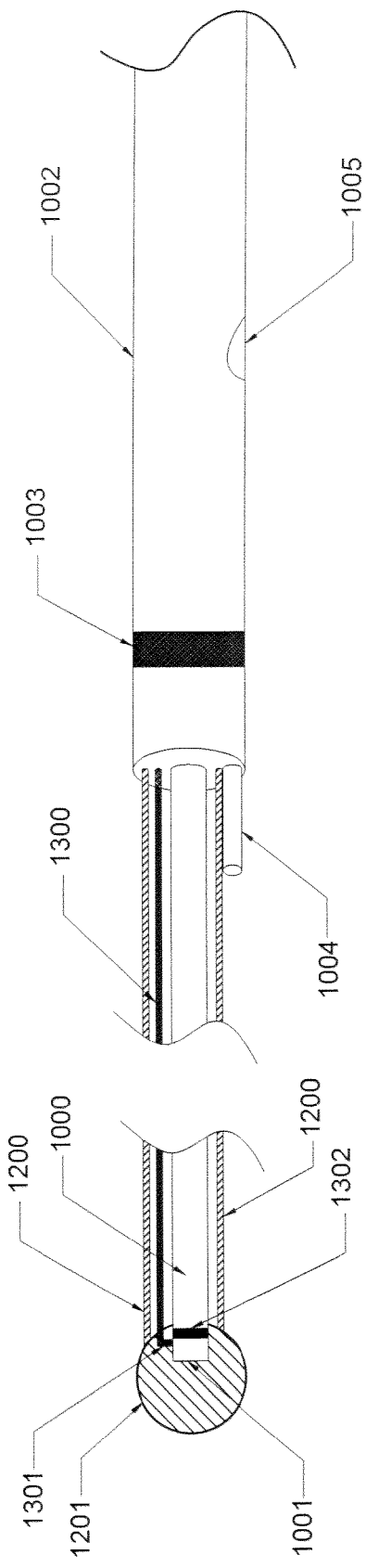

FIG. 13 shows another alternative assembly of the ultrasound transmission member 1000. As previously mentioned, the ultrasound transmission member 1000 has a smaller cross sectional area along its length than at the proximal end 1100. Also, the ultrasound transmission member 1000 may include several narrowed regions to amplify energy propagation. Such a structure is prone to stress concentration along the ultrasound transmission member 1000 that may cause fracture or breakage thereof. Several measures may be taken to avoid such breakage, including increasing the size of the ultrasound transmission member 1000, and using energy pulsing or modulation to mitigate stress concentration, among others. However, in case the ultrasound transmission member 1000 breaks, parts of the ultrasound transmission member 1000 may be left behind in the patient's body even when the ultrasound transmission member is protected by the polymer sheath 1200 shown in FIG. 12. To address such a possibility, an anchor member 1300 can be extended along the ultrasound transmission member 1000 and attached at an attachment point 1301 to the distal end 1001 of the ultrasound transmission member 1000. At the proximal end, the anchor member 1300 may be attached to the ultrasound transmission member 1000, the catheter 1002, the connector 1006, or the proximal knob 1010 shown in FIGS. 10 and 11, or to the proximal end 1100 shown in FIG. 11. The anchor member 1300 will ensure that the ultrasound transmission member 1000 can be entirely removed from the patient's body in the case of breakage of the ultrasound transmission member 1000. The anchor member 1300 may be made of metal, polymer or combination of both. A radiopaque marker 1302 may be attached at the distal end of the ultrasound transmission member 1000 if required to provide radiopacity at the distal tip 1001. Attachments of the anchor member 1300 and radiopaque marker 1302 can be done by conventional methods such as bonding, welding, soldering, and crimping, among other. The distal tip 1001 may be further covered with the polymer shell 1201 on the distal-most end to encapsulate the radiopaque marker 1302, the distal portion of the anchor member 1300, the attachment 1301, and the distal tip 1001 itself. In addition, the polymer sheath 1200 may be extended along the ultrasound transmission member 1000 and the anchor wire 1300 to mitigate transverse vibrations of the ultrasound transmission member 1000. The construction of the catheter 1002 can be similar to one shown in FIG. 12, and include the radiopaque marker 1003, and the guidewire lumen 1004 having a proximal exit port 1005.

FIG. 14 shows another alternative structure of the ultrasound transmission member 1000. An additional metallic tip 1400 can be attached to the distal end 1001. Such a metallic tip may be helpful for crossing tight stenosis and recanalization of Chronic Total Occlusions (CTO) which often will have a well-organized and hardened composition that is otherwise impossible to cross with conventional guidewires. The devices in the embodiments described above may not always be suitable for such applications because the plastic shell 1201 shown in FIGS. 12 and 13 may be easily damaged while interfacing or crossing hard calcific plaque. A radiopaque marker 1302 is also attached to the ultrasound transmission member 1000. If the metallic tip 1400 is sufficiently radiopaque, the radiopaque marker 1302 may not be necessary. The radiopaque marker 1302 may also be attached directly to the metallic tip 1400. An anchor member 1300 can also be attached to the tip 1001, and the polymer sheath 1200 and polymer shell (if necessary) may be attached in a similar fashion as shown in FIGS. 12 and 13. The anchor member 1300 may also be attached to the metallic tip 1400 at the attachment point 1301. The construction of the catheter 1002 can also be similar to constructions shown in FIGS. 12 and 13, and can include the radiopaque marker 1003, and the guidewire lumen 1004 having a proximal exit port 1005.

FIG. 15 illustrates the ultrasound transmission member 1000 shown in FIG. 14, and in use with an additional catheter 1500 that is positioned around the ultrasound transmission member 1000 and around the catheter 1002. The additional catheter 1500 may serve an aspiration purpose as illustrated with arrows 1501, either to remove ablated tissue, therapeutic drug after use, blood clots or irrigation provided for cooling of the ultrasound transmission member 1000 during ultrasound energy delivery. The aspiration catheter 1500 may be positioned along the distal end of the catheter 1002 and the ultrasound transmission member 1000 as needed to safely and effectively apply ultrasound energy to the treated area while removing ablated tissue, therapeutic drug after use, blood clots or irrigation material. A further alternative may be to provide a single catheter with two lumens that can perform the same functions as the catheter 1002 and the aspiration catheter 1500 (not shown). The aspiration catheter 1500 can be made of a polymer tube, metal tube or combinations of both. The use of aspiration and ultrasound energy producing surface waves at the same time may be particularly beneficial for removing blood clots or thrombus from the patient's body. Examples of blood clots removal includes locations within the endovascular system and outside of the endovascular system, but are not limited to Arterial and Venous Thrombolysis, Isehemic and Hemorrhagic Stroke. Deep Vein Thrombolysis (DVT). Pulmonary Embolism and any other cavities in human body where blood clots needs to be removed including organs and the head. Removing tissue, blood clots or liquids may be achieved by various configurations/locations of the ultrasound transmission member 1000 and the catheter 1002 in respect to the aspiration catheter 1500. The ultrasound transmission member 1000 may be exposed outside of the catheter 1002 at a length that is clinically necessary, and such range may be between 0.1 mm and 500 mm. During blood-clot removal or other tissue removal, the ultrasound transmission member 1000 and/or the catheter 1002 may be positioned outside of the aspiration catheter 1500 as shown in FIG. 15. Also, in another embodiment, the ultrasound transmission member 1000 and the catheter 1002 may be positioned fully inside the aspiration catheter 1500 (not shown). In such case, aspiration pressure will suck or extract blood clots or other tissue inside the catheter 1500 as shown by arrows 1501. Once blood clots or other removed tissue reach entry into the catheter 1500, it is macerated and dissolved by ultrasound energy generated from the ultrasound transmission member 1000 to facilitate continuous tissue removal. In such case, the ultrasound in the form of longitudinal and surface waves liquefies blood clots and removed tissue to further prevent the catheter 1500 from clogging and obstruction. Aspiration may be provided by vacuum pump(s) that are separate from the system shown on the FIG. 1, or such a vacuum pump(s) may be incorporated in the generator 160.

Devices shown in FIGS. 10-15 may also be used to treat heart valve stenosis and restenosis including calcifications. Calcification of heart valves often preclude effective valvuloplasty, and in such case ultrasound devices can be used to change compliance of the calcified portion of the treated heart valve by inducing cracks and micro-channels to further facilitate effectiveness of valvuloplasty. Use of therapeutic drugs to treat stenosis and restenosis of heart valves may also be advantageous for a better longer term clinical results.

FIG. 16A illustrates an aortic valve having diseased leaflets 1600, left ventricular outflow track 1601, valve annulus 1602, aortic sinus 1603, and aortic wall 1604. An ultrasound catheter 902 having a radiopaque marker 905, a transmission member 903 and a distal tip 904 as shown in FIG. 14 is positioned within the diseased heart valve leaflets 1600. Ultrasound energy in form of radial waves 908 is delivered from the transmission member 903 to the leaflets 1600, causing change in compliance by inducing micro-channels and micro-cracks in both stenotic tissue and in calcifications. This improves the effect of aortic valvuloplasty, and increases the permeability of the leaflets 1600. The duration of ultrasound exposure should be greater than 1 second and not to exceed 60 minutes. The ultrasound catheter 902 is usually introduced to the treatment area through a femoral or brachial artery over a guidewire (not shown) using techniques that are well known in the art.

FIG. 16B illustrates an aortic valvuloplasty catheter 1605 having a catheter shaft 1606, an aortic dilatation balloon 1607, and a distal tip 1608. The catheter 1605 is introduced through the same femoral or brachial artery (not shown) over a guidewire 1609. As the balloon 1607 is inflated with contrast media, the leaflets 1600 are pressed against the wall of aortic sinus 1603. It may be necessary to inflate and deflate the aortic balloon 1607 several times to achieve the desired flexibility in the valve leaflets 1600. Application of ultrasound energy to the leaflets maybe done prior to performing valvuloplasty, or after valvuloplasty. Examples of aortic balloons include but are rot limited to the V8™ Aortic Valvuloplasty Balloon Catheter (InterValve Inc. Minnetonka, Minn.).

FIG. 16C illustrates a dual balloon occlusion catheter 1610 having a catheter shaft 1611, two compliant balloons 1612A and 1612B, and a distal tip 1613. The catheter 1610 is positioned over the guidewire 1614 between the heart valve leaflets 1600. The dual balloon catheter 1610 provides protection during delivery of antistenotic drugs, so that therapeutic drug does not flow down the blood stream, but is applied to the leaflets 1600. The dual balloon catheter 1610 also has a distal shaft 1615 located between the balloons 1612A and 1612B. A drug outlet 1616 is situated on the distal shaft 1615 and serves to deliver therapeutic agents into the space between the balloons 1612A and 1612B. Therapeutic drug 1617 delivered through the outlet 1616 is applied to the valve leaflets 1600. The therapeutic drug 1617 is delivered under pressure from the outlet 1616 into the space between the balloons 1612A and 1612B, causing the valve leaflets 1600 to open and be fully exposed to the therapeutic drug 1617. The therapeutic drugs should be applied to the valve leaflets for a duration ranging between 1 second and 60 minutes. An example of a dual balloon catheter that can be used herewith may include but is not limited to the TAPAS™ Catheter (Spectranetics Corp., Colorado Springs, USA).

If needed, prior to the steps described in FIGS. 16A, B, C, the tip 904 can be used to decalcify the surface of the leaflets 1600 by repositioning the ultrasound catheter 902 and the transmission member 903 to a desired treatment location and performing calcification removal (e.g. by ablation). An additional sheath may be used around the ultrasound catheter 902 to aspirate any particles created by ablation of calcific and non-calcific tissue from the leaflets.

Also the scope of the invention incorporates delivery of ultrasound energy to the vessel wall before, during and after delivery of the therapeutic agent. Drug delivery may be achieved using ultrasound drug delivery catheters or any separate drug delivery device. Drug delivery may also be achieved with intravenous drug delivery or with endovascular methods using ultrasound drug delivery catheters or any separate drug delivery device.

To achieve the required therapy effects, it is desirable to apply ultrasound energy while most of the therapeutic drug is still present at the treatment area. If the therapeutic drug is delivered first, it would be advantageous to deliver ultrasound energy to the treatment area within a short period of time after the drug has been applied. If ultrasound energy is delivered first to the treatment area, the effect of ultrasound to enhance drug permeability lasts from the time when energy is delivered, and is usually no longer than 60 minutes after ultrasound energy is exposed to the vessel wall.

Other alternative embodiments of devices and methods for the present invention include delivery of the therapeutic drug intravenously (IV) and enhancing permeability of the vessel wall via the delivery of ultrasound energy to the treatment location. Ultrasound energy delivery will induce local vasodilatation and sonoporation within the surrounding tissue, further increasing drug uptake. Ultrasound energy may be emitted to the treatment area using transcutaneous (from outside of the body) or endovascular catheter methods. IV delivery of drug will cause a systemic effect causing the entire blood system to carry the therapeutic drug. By using a targeted ultrasound energy that is limited to a specific treatment area, the applied drug penetrates into the vessel wall of the treatment area more effectively. Emission of ultrasound energy and IV delivery of the therapeutic drugs can be administered in a variety of combinations: the therapeutic drug may be delivered intravenously either before delivery of ultrasound energy to the treatment area, during delivery of ultrasound energy or after delivery of ultrasound energy to the treatment area. In addition, a treatment area may be exposed to any other interventional procedure, including but not limited to: balloon angioplasty or venoplasty, stent placement, atherectomy, laser procedure, cryoplasty, other drug delivery and any combination of such procedures. Any interventional procedure may take place either before, during or after ultrasound/drug therapy. Further enhancement of the therapeutic drug uptake in the treatment area may be achieved using distal, proximal or dual flow protection or flow limitation devices such as compliant or non-compliant balloon devices. Therapeutic drug(s) delivered through the IV approach may be mixed with a conventional saline or any suitable contrast medium.

Still other alternative embodiments of devices and methods of the invention include delivery of ultrasound energy to a treatment area and delivery of therapeutic agent(s) that are mixed with a suitable contrast medium. The concept of using contrast media as a matrix for antiproliferative drugs delivery can simply employ standard endovascular angiography techniques. The contrast medium is chosen as the vehicle for therapeutic drug delivery because it significantly enhances the solubility of the drugs that are usually not easily solvent in conventional saline. Examples of suitable contrast medium include but are not limited to: Omnipaque 300. Amersham Health, N.J., USA; Ultravist-300. Schering AG. Berlin, Germany and NIOPAM 300. Bracco UK Limited. Ultrasound energy delivery will induce local vasodilatation and sonoporation within the vessel wall, further increasing permeability of the drug delivered with contrast medium. Ultrasound energy may be delivered to tie treatment area using transcutaneous methods (from outside the body) or endovascular catheter methods. Delivery of therapeutic drugs to the treatment area can be administered in a variety of combinations; therapeutic drug may be delivered either before delivery of ultrasound energy to the treatment area, during delivery of ultrasound energy to the treatment area, or after delivery of ultrasound energy to the treatment area. Therapeutic drug may be delivered by the ultrasound catheter that is energized or not energized, by a separate drug delivery catheter or through a conventional medium injection into a percutaneous sheath. In addition, a treatment area may be exposed to any other interventional procedure including but not limited to; balloon angioplasty or venoplasty, stent placement, atherectomy, laser procedure, ultrasound angioplasty or venoplasty, cryoplasty, other drug delivery and any combination of such procedures. Any interventional procedure may take place either before, during or after ultrasound/drug therapy. Further enhancement of the therapeutic drug uptake in the treatment area may be achieved using distal, proximal or dual flow protection or flow limitation devices, such as for example, compliant or non-compliant balloon devices.

Another embodiment of the present invention includes delivery of ultrasound energy to a treatment area and delivery of therapeutic agent(s) that are mixed with Carbamide. Carbamide is an organic compound with the chemical formula $(NH_2)_2CO$. The molecule has two amine ($-NH_2$) groups joined by a carbonyl ($C=O$) functional group, and is also known as urea. Urea serves an important role in the metabolism of nitrogen-containing compounds by animals and is the main nitrogen-containing substance in the urine of mammals. It is solid, colourless, and odorless. It is highly soluble in water and non-toxic. Dissolved in water, it is neither acidic nor alkaline. The body uses it in many processes, most notably nitrogen excretion. Carbamide can be synthesized in the lab without biological materials. It has been hypothesized that Carbamide may be a good and effective solvent to dilute Paclitaxel for use in anticancer and antistenosis therapy.

While the ultrasound delivery methods above describe transcutaneous transducers that are located outside the body (for example, U.S. Pat. No. 6,398,772 (Bond et al.)) and endovascular transducers located on the proximal end of the catheter (for example, U.S. Pat. No. 5,342,292 (Nita et al.)), use of small endovascular transducers located at the distal end of the catheter is also possible. Examples of such distal transducers are illustrated in U.S. Pat. No. 5,728,062 (Brisken), U.S. Pat. No. 6,001,069 (Tachibana et al.), U.S. Pat. No. 6,372,498 (Newman et al.). U.S. Pat. No. 6,387,116 (McKenzie et al.), U.S. Pat. No. 6,432,068 (Corl et al.), U.S. Pat. No. 6,484,052 (Visuri et al.), and U.S. Pat. No. 6,723,063 (Zhang et al.), and these disclosures are hereby incorporated by this reference as though set forth fully herein. The use of ultrasound energy to disrupt clots and to enhance delivery of drugs to clots has been recently proposed using a flexible probe, where the entire length of the probe forms a cutting surface to ablate unwanted tissue in the transverse mode of operation. Examples of such flexible probes are illustrated in U.S. Pat. Nos. 6,551,337, 6,652,547 and 7,494,468, which solely relays transverse motions of the flexible probe, and these disclosures are hereby incorporated by this reference as though set forth fully herein.

The development of thrombosis as a result of vessel injury or delayed endothelialization is a recognized risk of transcutaneous or endovascular intervention with some therapeutic agents that may be used to prevent restenosis. In such cases, administration of the appropriate medication may be required.

Ultrasound energy delivered for stenosis and restenosis therapies either in endovascular or transcutaneous fashion may be generated or produced by longitudinal sound waves, transverse sound waves, radial sound waves, or combination of these sound waves.

Although the invention has been described above with respect to certain embodiments, it will be appreciated that various changes, modifications, deletions and alterations may be made to such above-described embodiments without departing from the spirit and scope of the invention. Accordingly, it is intended that all such changes, modifications, additions and deletions be incorporated into the scope of the following claims. More specifically, description and examples have been provided that relate to treatment of stenotic arterial sites and to therapeutic agents that are appropriate for treating such sites. However, the scope of the invention includes the application of these methods to treating sites other than stenotic sites, and to facilitating the intracellular delivery of any therapeutic agent appropriate for treating the particular target site.

Some theoretical considerations have been provided as to the mechanism by which these therapeutic methods are effective; these considerations have been provided only for the purpose of conveying an understanding of the invention, and have no relevance to or bearing on claims made to this invention.

The invention claimed is:

1. A method of treating vascular stenosis, comprising the steps of:
performing balloon angioplasty at a treatment area inside a vessel;
positioning a distal end of a vibrational device at the treatment area, the vibrational device having a transmission member;

propagating vibrational energy through the transmission member from a proximal transducer located outside the patient to the distal end of the vibrational device at a frequency of 1 KHZ-20 MHZ while undergoing irrigation to form surface waves at the distal end of the vibrational device;

applying the surface waves at a power of less than 20 Watts at the distal end of the vibrational device to the treatment area to change the stenosis compliance and to increase permeability of the vessel for delivery of an anti-proliferative agent, wherein the surface waves are propagated from the distal end of the vibrational device to the treatment area through irrigation liquid;

positioning a blood flow protection device at a location distal to the treatment area to prevent the anti-proliferative agent from flowing distally;

delivering the anti-proliferative agent to the treatment area using a contrast agent as a matrix within less than 60 minutes from the application of the surface waves; and applying the therapeutic agent in the treatment area for less than 60 minutes.

2. The method of claim 1, further including performing an interventional procedure that is selected from the group consisting of: stent placement, atherectomy, laser, ultrasound, cryoplasty, and a combination thereof.

3. The method of claim 1, wherein the anti-proliferative agent in mixture with contrast further includes saline solution.

4. The method of claim 1, further including delivery of longitudinal waves, transverse waves, and a combination thereof.

5. The method of claim 1, wherein vibrational energy is propagated from the vibrational device to the treatment area in one of the following ways: through irrigation liquid in mixture with blood, through direct contact with the tissue, and combination of all.

6. The method of claim 1, further comprising at least partially removing the anti-proliferative agent outside the body.

7. The method of claim 1, further including the treatment of endovascular stenosis in one of the following treatment areas: arteries, veins, in-stent, grafts, fistulas, or combinations thereof.

8. The method of claim 1, wherein the blood flow protection device is a first blood flow protection device, further including positioning a second blood flow protection device proximally to the treatment area.

9. The method of claim 8, wherein the first and second blood flow protection devices comprise a dual balloon device having a first balloon adjacent a distal end of the treatment area and the second balloon adjacent a proximal end of the treatment area.

10. The method of claim 1, wherein the vibrational device includes a flexible member located on the distal end.

11. The method of claim 1, wherein the vascular stenosis includes a chronic total occlusion.

12. The method of claim 1, wherein treating vascular stenosis includes treating vulnerable plaque.

13. The method of claim 1, further including applying vibrational energy to the treatment area at one of the following times: before balloon angioplasty, during balloon angioplasty, after balloon angioplasty, before drug application, during drug application, after drug application, or a combination thereof.

14. The method of claim 1, wherein the balloon angioplasty and blood flow protection are performed with the same device.

15. The method of claim 1, wherein the anti-proliferative agent is Paclitaxel.

16. A method of treating vascular stenosis, comprising the steps of:

performing balloon angioplasty at a treatment area inside a vessel;

positioning a vibrational device at the treatment area, the vibrational device having a transmission member;

propagating vibrational energy through the transmission member from a proximal transducer located outside the patient to the distal end of the vibrational device at a frequency of 1 KHZ-20 MHZ while undergoing irrigation to form surface waves at the distal end of the vibrational device;

applying the surface waves at a power of less than 20 Watts at the distal end of the vibrational device to the treatment area to change the stenosis compliance and to increase permeability of the vessel to receive an anti-proliferative agent, wherein the surface waves are propagated from the distal end of the vibrational device to the treatment area through irrigation liquid;

delivering an anti-proliferative agent to the treatment area using a drug delivery balloon device within less than 60 minutes from the application of the surface waves; and applying the anti-proliferative agent in the treatment area for less than 60 minutes.

17. A method of treating vascular stenosis, comprising the steps of:

performing balloon angioplasty at a treatment area inside a vessel;

positioning a vibrational device at the treatment area, the vibrational device having a transmission member;

propagating vibrational energy through the transmission member from a proximal transducer located outside the patient to the distal end of the vibrational device at a frequency of 1 KHZ-20 MHZ and a power of less than 20 Watts while undergoing irrigation to form surface waves at the distal end of the vibrational device;

applying the surface waves from the vibrational device to the treatment area to change the stenosis compliance and to increase permeability of the vessel to receive an anti-proliferative agent, wherein the surface waves are propagated from the distal end of the vibrational device to the treatment area through irrigation fluid;

delivering an anti-proliferative agent to the treatment area within less than 60 minutes from the application of the surface waves; and delivering a drug eluting stent within less than 60 minutes from the application of the surface waves.

* * * * *